(12) United States Patent
Furusawa

(10) Patent No.: US 6,755,844 B2
(45) Date of Patent: Jun. 29, 2004

(54) LIGATOR

(76) Inventor: Akihito Furusawa, 6-20, Nishinaka-machi, Ube-shi, Yamaguchi-ken (JP)

( * ) Notice: Subject to any disclaimer, the term of this patent is extended or adjusted under 35 U.S.C. 154(b) by 155 days.

(21) Appl. No.: 09/842,193

(22) Filed: Apr. 26, 2001

(65) Prior Publication Data

US 2001/0041901 A1 Nov. 15, 2001

(30) Foreign Application Priority Data

Apr. 27, 2000 (JP) .................................. P2000-127807

(51) Int. Cl.[7] .............................................. A61B 17/12
(52) U.S. Cl. ...................................................... 606/144
(58) Field of Search ................... 606/144, 138, 606/139, 228, 148, 145, 146, 147; 289/1.5, 2, 17

(56) References Cited

U.S. PATENT DOCUMENTS

| | | | | |
|---|---|---|---|---|
| 2,610,631 A | * | 9/1952 | Calicchio | 128/326 |
| 3,752,516 A | * | 8/1973 | Mumma | 289/17 |
| 4,602,635 A | * | 7/1986 | Mulhollan et al. | 128/334 R |
| 4,961,741 A | * | 10/1990 | Hayhurst | 606/139 |
| 5,176,691 A | * | 1/1993 | Pierce | 606/148 |
| 5,334,200 A | * | 8/1994 | Johnson | 606/148 |
| 5,397,326 A | * | 3/1995 | Mangum | 606/148 |
| 5,609,597 A | * | 3/1997 | Lehrer | 606/139 |
| 6,200,329 B1 | * | 3/2001 | Fung et al. | 606/232 |
| 6,235,040 B1 | * | 5/2001 | Chu et al. | 606/139 |
| 6,280,452 B1 | * | 8/2001 | Mears | 606/140 |
| 6,358,259 B1 | * | 3/2002 | Swain et al. | 606/148 |

FOREIGN PATENT DOCUMENTS

JP            05-317321            3/1993

* cited by examiner

Primary Examiner—John J. Calvert
Assistant Examiner—Alissa L. Hoey
(74) Attorney, Agent, or Firm—Rader, Fishman & Grauer PLLC; Ronald P. Kananen, Esq.

(57) ABSTRACT

A ligator comprises a ligation member formed of a bar-shaped body having a constant thickness in a region extending by at least prescribed length from one end of the ligation member. The ligation member has a front hole and a pair of side holes. The front hole is formed on one end surface of the ligation member. The front hole has a prescribed shape and a prescribed depth in the longitudinal direction of the ligation member. The pair of side holes are formed on opposite positions at one end portion of the ligation member so as to be substantially at right angles to the front hole. The front hole is located between the opposite positions. The side holes communicating with the front hole. The opposite ends of a ligature to be knotted passes through the front hole and the side holes.

20 Claims, 22 Drawing Sheets

LIGATOR

BACKGROUND OF THE INVENTION

1. Field of the Invention

The present invention relates to a ligator used to knot a ligature in a body in a medical care, i.e., surgery, especially endoscopic surgery.

2. Description of the Related Art

A technique to make an incision portion smaller in surgery is regarded as important in order to accelerate the course of convalescence after an operation and make an operative wound left in a body smaller. Recently, endoscopic surgery permitting to make an incision portion excessively smaller has widely been put into practical use.

In such endoscopic surgery, there is required an operation to carry out ligation of tissue or a blood vessel in a body with the use of a ligature or to knot the ligature after suture to fix the sutured portion by an operator through a minor opening of an incision of the body. A medical appliance called a "ligator" has conventionally been used to achieve such an operation of knotting the ligature in the body from outside thereof. Japanese Provisional Publication No. HEI 05-317321 discloses one of examples of such a conventional ligator, which is illustrated in FIGS. 21 and 22. FIG. 21 is a schematic descriptive view of the conventional ligator and FIG. 22 is a cross-sectional view of essential elements of the conventional ligator.

The conventional ligator 100 as shown in FIGS. 21 and 22 comprises a handle 101 having a prescribed length, a recess portion 102 formed on the front end of the handle 101, a guide passage 103 provided so as to communicate with the recess portion 102 and extend beyond the bottom of the recess portion 102 between the opposite portions thereof toward the front end of the handle 101.

Description will be given below of a ligation operation using the conventional ligator 100. A ligature 50 is previously put around a target part in a body, which is to be subject to a ligation operation (i.e., tissue in the body, a blood vessel, or the like) (hereinafter referred to as the "target regation part in the body") and the opposite ends of the ligature 50 are pulled out of the body with the use of another medical appliance. An operator crosses the opposite ends of the ligature 50 to make a half hitch 51 outside the body. Opposite portions of the ligature 50 extending from the half hitch 51 are put in the guide passage 103 in the vicinity of the recess portion 102. The operator moves the ligator 100 forward while holding the opposite ends of the ligature 50. As a result, the half hitch 51 shifts to move together with the front end of the ligator 100, while the ligature 50 smoothly slips in the guide passage 103 without occurrence of contact of the half hitch 51 with the recess portion 102 of the ligator 100. The ligator 100 is inserted into the body in such a state to move the half hitch 51 toward the target regation part in the body. After the half hitch 51 finally moves to the above-mentioned target part in the body, the opposite ends of the ligature 50 are pulled from outside the body to make a knot, while keeping the ligator 100 stationarily, thus providing a ligation condition for the target part in the body.

In the conventional endoscopic surgery, a port is used to be fixed to the surface of a body to facilitate insertion of a medical appliance such as the ligator into the body and removal of it from the body (see FIG. 1). A closed-type port, which is used in the endoscopic surgery according to aeroperitoneum, has a built-in valve for preventing occurrence of a gas leakage. A ligature that is put around a target part in the body, which is to be subject to a ligation operation, and pulled out of the body, comes into contact with the valve, resulting in a bending state in the middle of the ligature. When the ligator 100 is inserted into such a port, the ligature may come off the guide passage 103 at one of the opposite portions between which the recess portion 102 is placed, due to the bending state of the ligature in the vicinity of the valve. This may cause the half hitch 51 to deviate from the recess portion 102, deteriorating slidability of the ligature 50 and causing a problem. When the ligator 100 opens the valve and enters the port, a resistance force having a function of returning the valve to close it is applied to the ligator 100. An operator cannot easily recognize that such a resistance force is generated due to deviation of the half hitch 51 of the ligature or returning action of the valve. This makes it unable to judge properly whether the operation be continued or not, causing the other problem.

In case where the operator continues to insert the ligator 100 without recognizing deviation of the half hitch 51 of the ligature 50, the ligature 50 may be broken or an excessively large force may be applied to the target regation part in the body, around which the ligature 50 has been put, thus causing damage. When the ligature 50 comes off the front end of the ligator 100 within the port, it is very difficult to put again the ligature 50 on the front end thereof due to impossibility of visual inspection of the inside of the port.

The conventional ligator 100 has a non-uniform thickness. There exists a relatively large gap between the port into which the maximum thickness portion of the ligator 100 can be inserted and the ligator 100 has actually been inserted into the port. This may cause an aeroperitoneum gas to leak out during operation, thus making it impossible to ensure a proper field of vision through an endoscope, resulting in interruption of operation.

SUMMARY OF THE INVENTION

An object of the present invention, which was made to solve the above-described problems, is therefore to provide a ligator, which prevents a ligature from coming off the front end of the ligator, has a shape of the front end thereof, by which the ligature can easily be put on the front end of the ligator even when it comes off, permits to shift surely a half hitch of the ligature toward a target part, which is to be subject to a ligation operation, and permits an operator to carry out the ligation operation so as to improve remarkably an operation efficiency, thus reducing a burden of both the operator and a person to be operated.

In order to attain the aforementioned object, a ligator of the present invention comprises a ligation member formed of a bar-shaped body having a constant thickness in a region extending by at least a prescribed length from one end of said ligation member; a front hole formed on one end surface of said ligation member, said front hole having a prescribed shape and a prescribed depth in a longitudinal direction of said ligation member; and a pair of side holes formed on opposite positions at one end portion of said ligation member so as to be substantially at right angles to said front hole, said front hole being located between said opposite positions, and said side hole communicating with said front hole, opposite ends of a ligature to be knotted passing through said front hole and said side hole. In the feature of the present invention, the bar-shaped ligation member is provided on its front end with the front hole and the side holes. An operator passes the opposite ends extending from a half hitch of a ligature through the front hole and the side holes so that the half hitch is placed within the front hole. The operator carries out a ligation operation while holding the opposite ends of the ligature. When the ligator is inserted into a body, the side holes urge the ligature to shift the half hitch of the ligature into the body, while keeping the half hitch within the front hole of the ligator. When the ligator is pulled out of the body, the ligature comes into contact with the ligation member within the front hole and the side holes to hold securely the ligature. It is therefore possible to pass the ligator through a port to carry out the ligation operation without causing deviation of the half hitch and slip-off of the ligature. In addition, the half hitch of the ligature shifts together with the front end of the ligator to prevent an excessively large force from being applied to the target part, which is to be subject to the ligation operation, thus improving safety. The ligation member is provided with a portion to be inserted into the body, which has a shape with substantially a constant thickness in the longitudinal direction of the ligation member. As a result, it is possible to make an opening of the port smaller, thus permitting to reduce a gas leakage ratio upon operation according to aeroperitoneum.

In the present invention, said ligation member may be provided, as an occasion demands, with a pair of recesses each connecting smoothly an inner surface of each of said side holes of said ligation member and an outer surface of said ligation member, each of said recesses being formed by chamfering an edge portion from said inner surface to said outer surface toward an other end of said ligation member. In such a feature of the present invention, the ligation member is provided with the recesses for connecting partially the outer surface of the ligation member and the inner surface of the side holes. A ligature received in the side hole is guided into the recess to reach the outside of the ligator, thus preventing the ligature from coming easily off the recess to secure a proper receiving state of the ligature within the side hole. The ligature does not come off the front end of the ligator so long as an operator holds the opposite ends of the ligature. In addition, when the ligator is inserted into a body, the ligature can smoothly move through the side hole toward the outside of the ligator, thus reducing contact resistance of the ligature with the ligation member. Accordingly, it is possible to carry out an insertion operation of the ligator in the body without causing slack of the ligature.

The ligation member of the present invention may be provided, as an occasion demands, with a gap portion, which causes said front hole to communicate with said side holes, said gap portion being formed by cutting a prescribed portion out of said ligation member, which faces said front hole and said side holes formed at the one end portion said ligation member and extends from the inner surface to the outer surface, said gap portion permitting said ligature to be received in said front hole and said side holes or removed therefrom. In such a feature of the present invention, the ligation member is provided at its one end portion with the gap portion through which the front hole and the side holes communicates with each other and these holes also communicate with the outside. Accordingly, it is possible to insert the ligature into the front hole and the side holes through the gap portion and to remove the ligature from these holes through the gap portion. It is therefore possible to carry out effectively an operation for inserting the ligature into the front hole and the side holes before starting a ligation operation as well as the other operation for removing the ligature from these holes after the completion of the ligation operation. As a result, a period of time required for the ligation operation can be reduced, and a burden of both the operator and a person to be operated upon can also be reduced.

The ligation member of the present invention may be formed, as an occasion demands, into a cylindrical shape having a hollow portion in said region extending by said at least prescribed length, said hollow portion forming said front hole. In such a feature of the present invention, the ligation member is formed into the hollow cylindrical shape in at least prescribed region so that the front hole is formed as a cylindrical space and the cross-section of the portion to be inserted into a body through the conventional port provides a symmetric shape. This makes it possible to reduce the gap between the port and the ligation member, thus permitting to reduce remarkably a gas leakage ratio upon operation according to aeroperitoneum.

In the ligator of the present invention, said gap portion may be formed, as an occasion demands, by cutting partially out of a peripheral portion of said ligation member, which comes into contact with said front hole and extends from one of said side holes to another of said side holes, and then removing at least a part of an end peripheral portion of said ligation member, which is placed along said peripheral portion thus cut, thereby said end peripheral portion forming a pair of arcuate projections. In such a feature of the present invention, the gap portion extends from the one side hole to the other side hole and further extends from the middle between the side holes to the one end surface of the ligation member so as to form a T-shape. As a result, the ligation member is provided on its one end portion with a pair of projections, which are defined by the gap portion, the front hole and the side holes. An operator can have the ligature caught by one or both of the projections before carrying out a ligature-insertion operation to obtain a state in which the ligature can be received in the front hole and the side holes. It is therefore possible to facilitate passing the ligature through the front hole and the side holes by handling of the ligator. It is therefore possible not only to carry out effectively an operation for inserting the ligature into the front hole and the side holes before starting a ligation operation as well as the other operation for removing the ligature from these holes after the completion of the ligation operation, but also to receive the ligature into the respective holes formed on the front end portion of the ligation member or remove it therefrom in a desired manner during a knot operation in the body, so as to make easily and appropriately an elaborate and ingenious operation, thus improving remarkably the operation efficiency in the body.

In the ligator of the present invention, there may be adopted, as an occasion demands, a structure in which said front hole extends beyond a position of each of said side holes by a prescribed length toward the other end side of said ligation member; and said ligator further comprises an inner tube, which is formed of a tubular member having a prescribed cross-section, which can be inserted into said front hole, said inner tube being slidably received in said front hole in the longitudinal direction of said ligation member from a position in which a front end of said tubular member is placed beyond said gap portion to reach the other end side of said ligation member to another position in which said tubular member closes at least a part of said gap portion from said front hole side to prevent said ligature received in said side holes from coming off said side holes through said gap portion. In such a structure of the present invention, the inner tube is provided in the front hole so as to be slidable in the longitudinal direction of the ligation member within a prescribed range. As a result, there can be selected any one of a number of modes, i.e., one mode in which the inner tube is moved to open the gap portion through operation of the operator so that the ligature-insertion or removal operation is permitted through the gap portion, and the other mode in which the inner tube is moved to close partially the gap portion so that any ligature-insertion or removal operation is not permitted. It is therefore possible to control the ligature to come in or out of the ligation member through the gap portion. This makes it possible to insert the ligator into the body and cause it to approach a target part in the body, to which is to be subject to a ligation operation, while preventing completely the ligature from coming off the gap portion. Accordingly, efficiency of an insertion operation of the ligator into the body can be remarkably improved, while maintaining an easy operation for inserting the ligature into the front hole and the side holes, thus remarkably reducing an operational burden of the operator.

In the ligator of the present invention, there may be adopted, as an occasion demands, a structure in which said ligation member is provided at said one end portion of said ligation member with two portions facing tip end portions of said pair of arcuate projections through said gap portion, at least one of said two portions having another recess connecting smoothly a prescribed portion of an end surface of said ligation member facing said gap portion and the outer surface of said ligation member, said other recess being formed by chamfering said prescribed portion of said end surface of said ligation member toward the outer surface of the other end side of said ligation member. In such a feature of the present invention, there is provided the other recess connecting partially the prescribed portion of the end surface of said ligation member facing said gap portion and the outer surface of said ligation member. When the ligature is brought into contact with the ligation member so as to be placed along the other recess portion, force having a function of pulling the ligature into the front hole is applied to the ligature, providing a state in which the ligature can easily be caught by the projection. Even when the ligature comes off the gap portion of the ligation member so as to be away from the ligation member in the body, the ligature can easily be caught by the projection to lead the ligature into the gap portion through operation of the operator, so as to return a proper state in which the ligature is received in the front hole and the side holes. It is therefore possible to carry out consecutively an operation for knotting the ligature in the body in an appropriate manner when the ligator is once inserted into the body. There is required no operation for inserting the ligator into the body and removing it therefrom several times to receive the ligature in the front hole and the side holes, permitting to smooth progress of the ligation operation without taking much time, thus remarkably reducing an operational burden of the operator.

The ligator of the present invention may further comprise, as an occasion demands, an opening or closing member, which is mounted on to said ligation member, said opening or closing member being movable to a position in which a part of said opening or closing member fits into said gap portion to close at least a part of said gap portion to prevent said ligature received in said side holes from coming off said side hole through said gap portion. In such a feature of the present invention, the opening or closing member is mounted movably on the ligation member so that there can be selected any one of a number of modes, i.e., one mode in which the opening or closing member is moved to open the gap portion through operation of the operator so that the ligature-insertion or removal operation is permitted through the gap portion, and the other mode in which the opening or closing member is moved to close the gap portion so that any ligature-insertion or removal operation is not permitted. It is therefore possible to insert the ligator into the body and cause it to approach a target part in the body, to which is to be subject to a ligation operation, while preventing completely the ligature from coming off the gap portion. Accordingly, efficiency of an insertion operation of the ligator into the body can be remarkably improved, while maintaining an easy operation for inserting the ligature into the front hole and the side holes, thus remarkably reducing an operational burden of the operator.

DETAILED DESCRIPTION OF THE PREFERRED EMBODIMENTS

First Embodiment of the Present Invention

Figure 1:
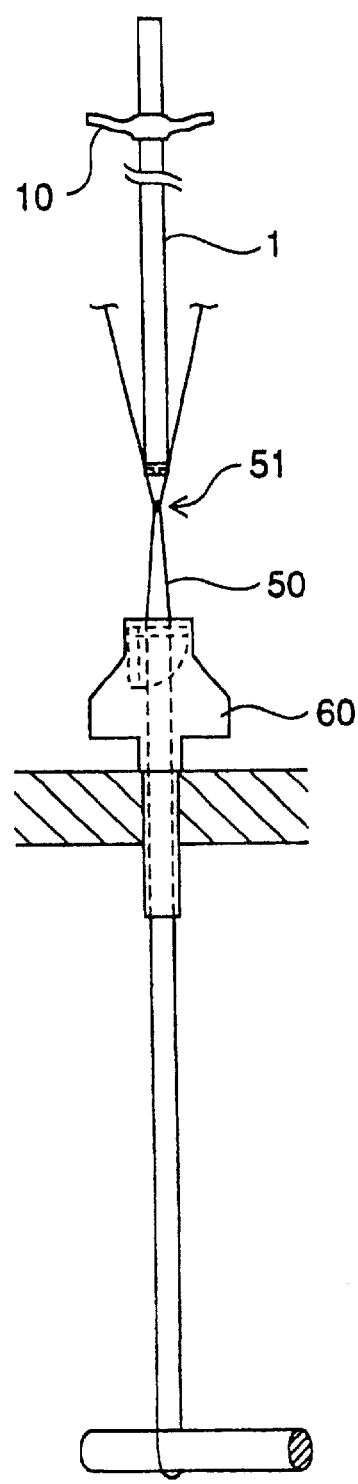
FIG. 1 is a descriptive view illustrating a used state of a ligator of the first embodiment of the present invention.
Figure 2:
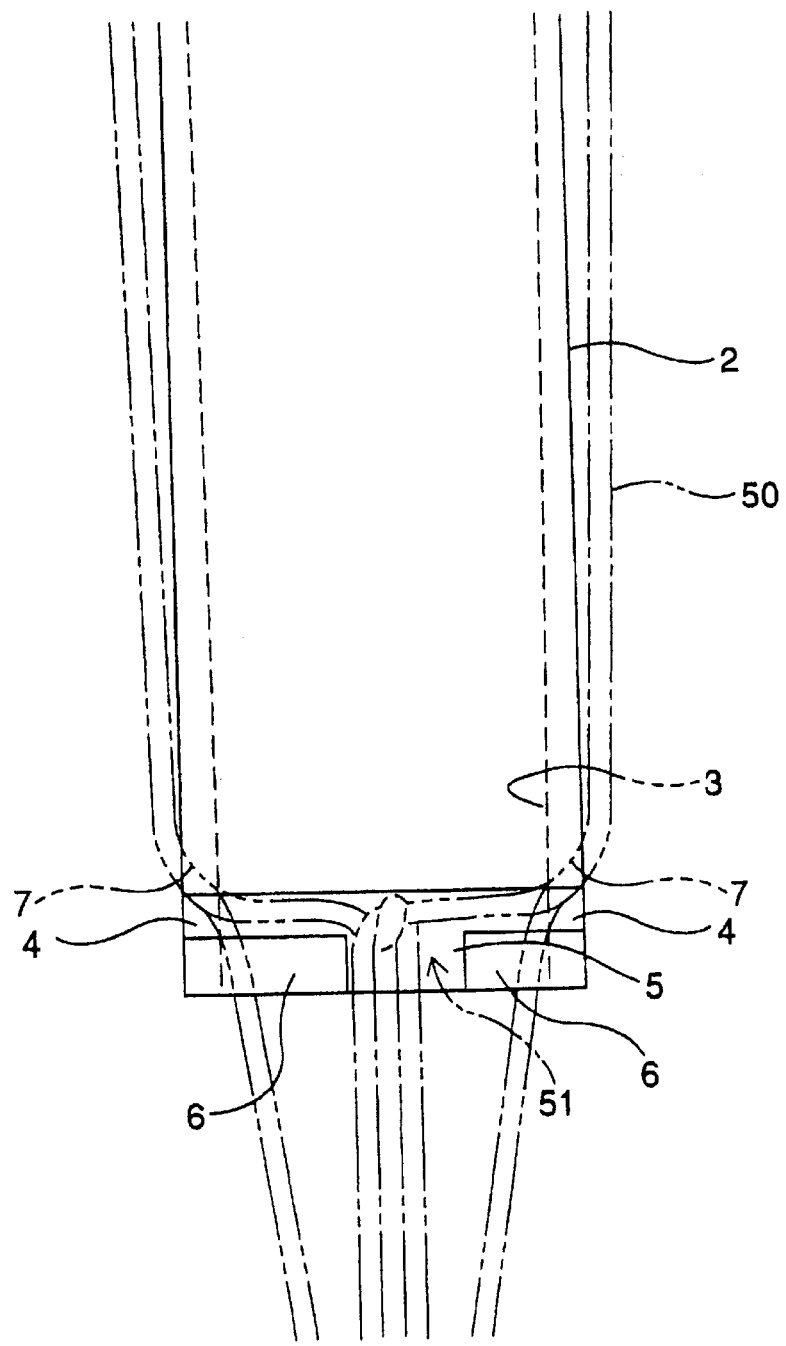
FIG. 2 is a partial front view illustrating the ligator of the first embodiment of the present invention.
Figure 3A:
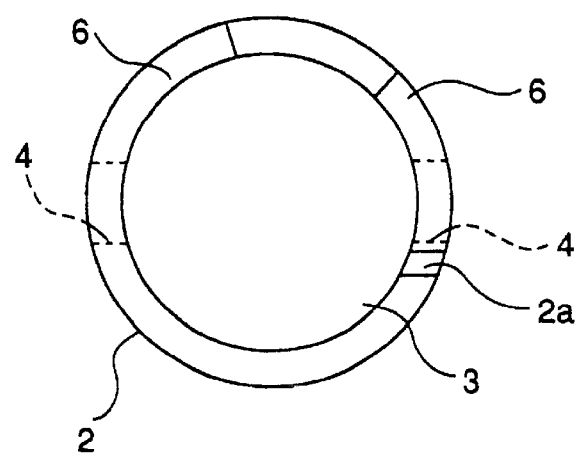
FIG. 3(A) is a bottom view illustrating the ligator of the first embodiment of the present invention and FIG. 3(B) is a partial side view illustrating the same ligator.
Figure 3B:
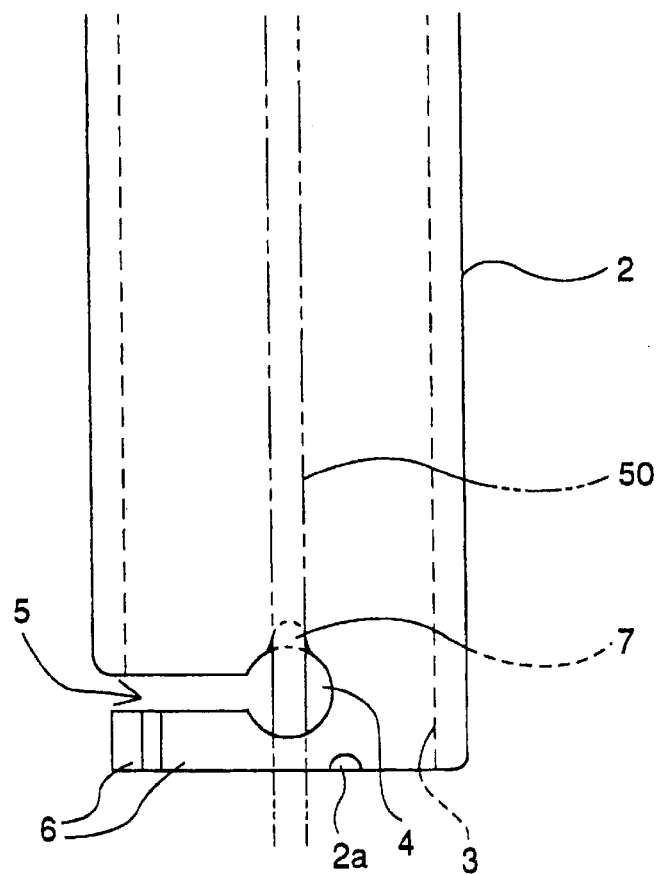
Figure 4A:
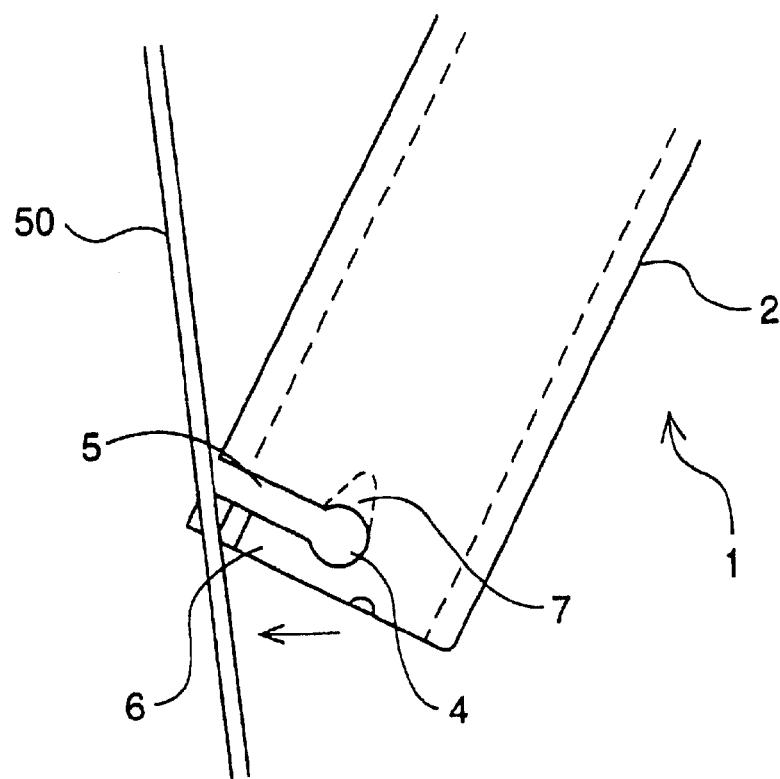
FIGS. 4(A) and 4(B) are views illustrating a state in which a ligature is inserted into the ligator of the first embodiment of the present invention.
Figure 4B:
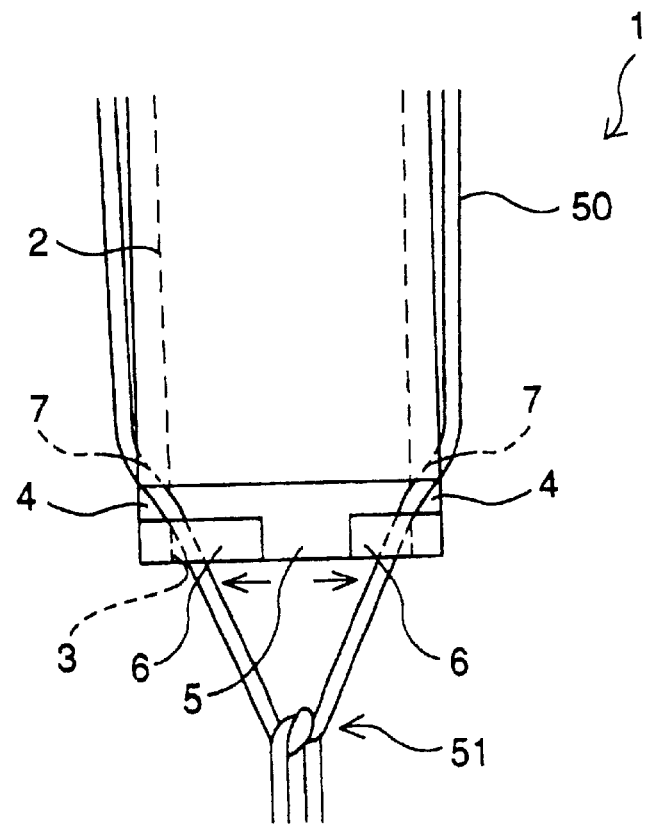
Figure 5A:
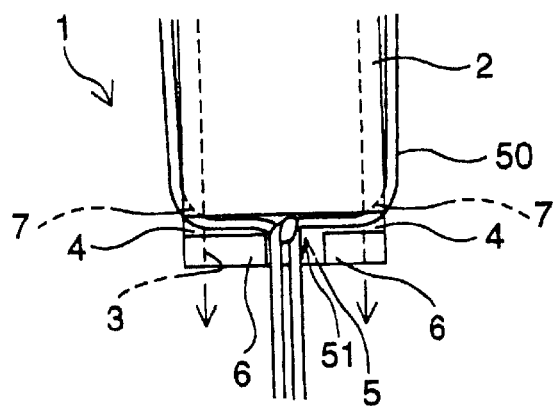
FIGS. 5(A), 5(B) and 5(C) are views illustrating a state in which the ligator of the first embodiment of the present invention is inserted into a body.
Figure 5B:
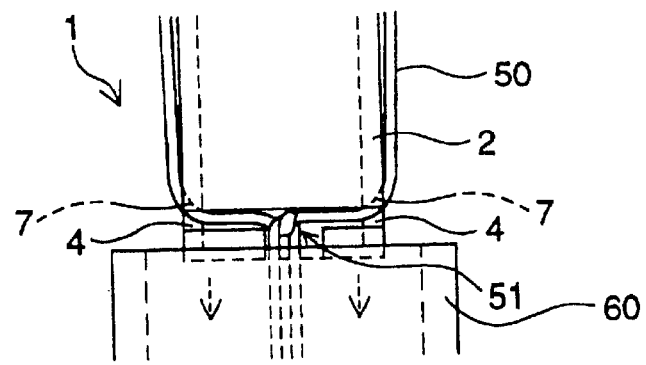
Figure 5C:
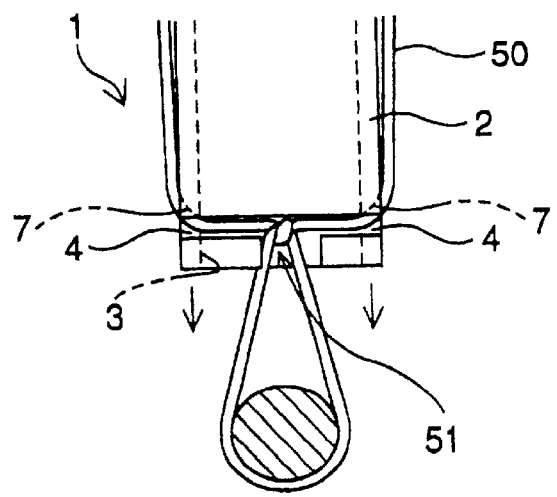
Figure 6A:
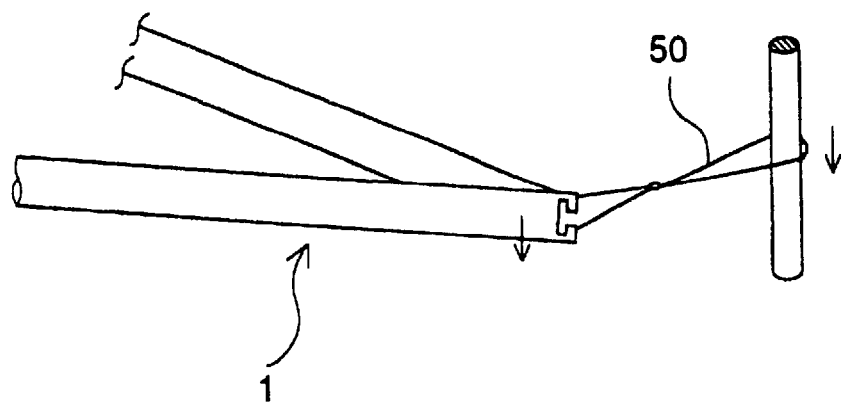
FIGS. 6(A) and 6(B) are views illustrating an operation for correcting a ligature-catching position with the use of the ligator of the first embodiment of the present invention.
Figure 6B:
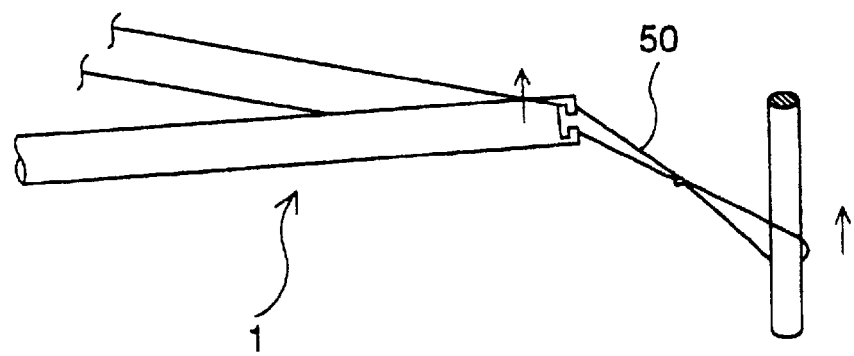
Figure 7A:
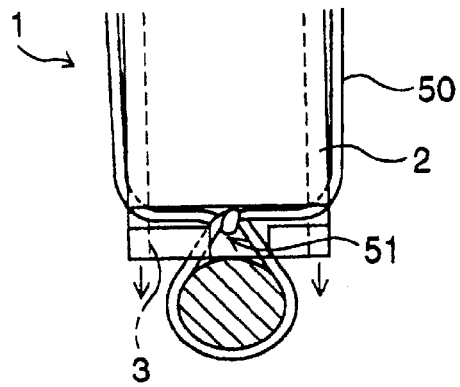
FIGS. 7(A), 7(B) and 7(C) are descriptive views illustrating a ligation operation with the use of the ligator of the first embodiment of the present invention.
Figure 7B:
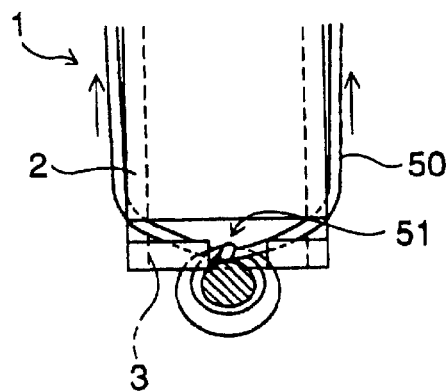
Figure 7C:
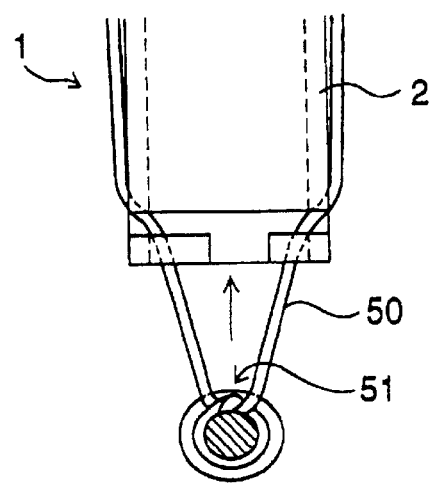
Figure 8A:
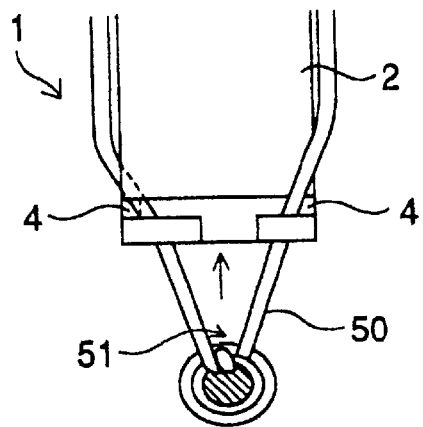
FIGS. 8(A), 8(B) and 8(C) are descriptive views illustrating the series of first half steps for making a half hitch of the ligature with the use of the ligator of the first embodiment of the present invention.
Figure 8B:
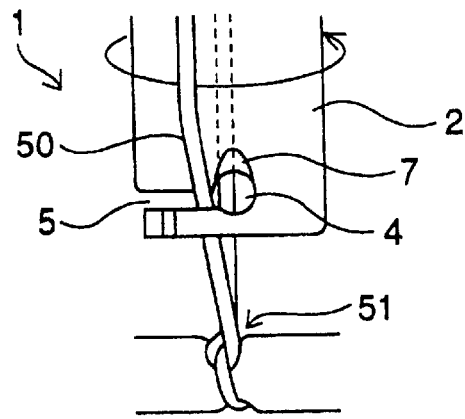
Figure 8C:
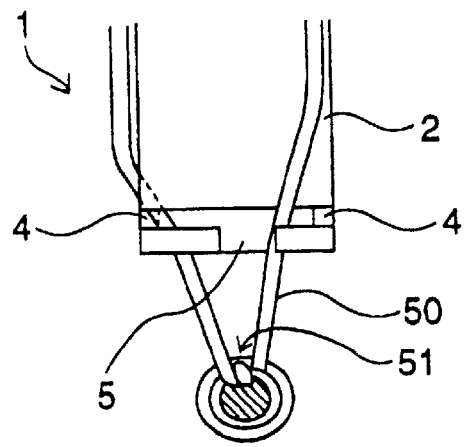
Figure 9A:
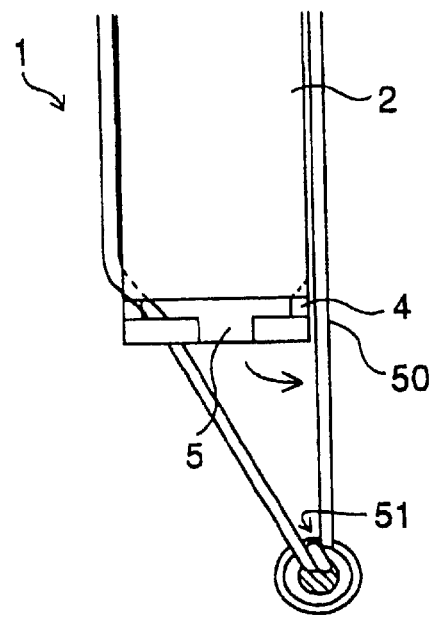
FIGS. 9(A) and 9(B) are descriptive views illustrating the series of second half steps for making the half hitch of the ligature with the use of the ligator of the first embodiment of the present invention.
Figure 9B:
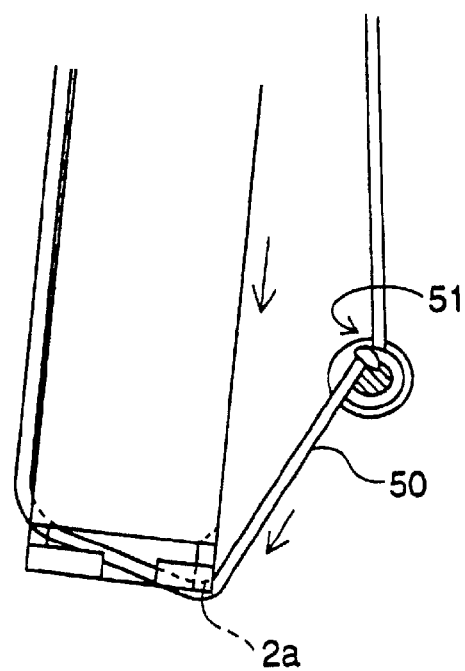
Figure 10A:
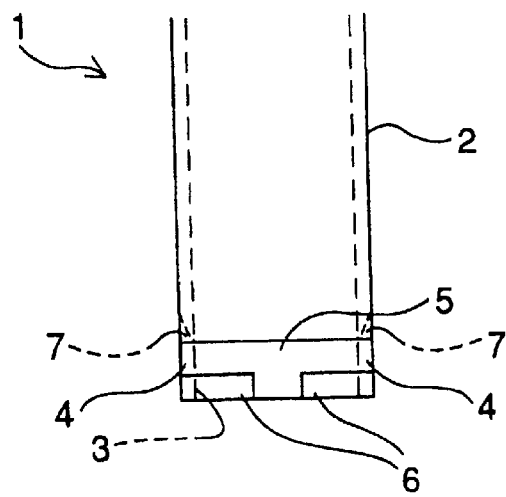
FIGS. 10(A), 10(B) and 10(C) are a partial front view, a bottom view and a partial side view illustrating the modified ligator of the first embodiment of the present invention, respectively.
Figure 10B:
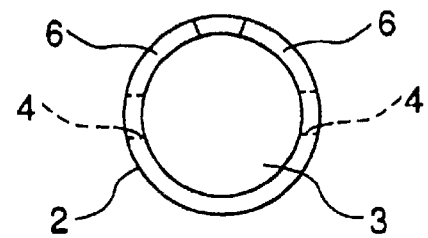
Figure 10C:
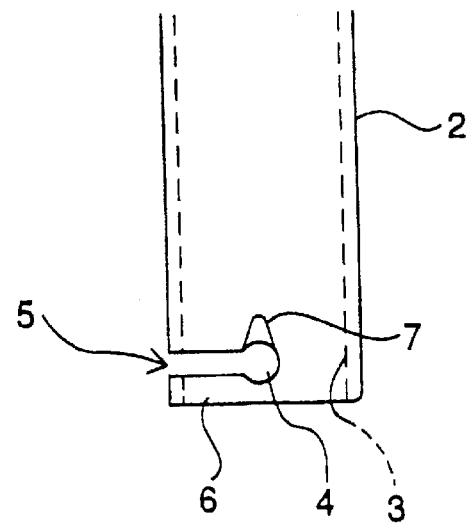

Now, a ligator of the first embodiment of the present invention will be described in detail below with reference to FIGS. 1 to 9. FIG. 1 is a descriptive view illustrating a used state of a ligator of the first embodiment of the present invention. FIG. 2 is a partial front view illustrating the ligator of the first embodiment of the present invention. FIG. 3(A) is a bottom view illustrating the ligator of the first embodiment of the present invention and FIG. 3(B) is a partial side view illustrating the same ligator. FIGS. 4(A) and 4(B) are views illustrating a state in which a ligature is inserted into the ligator of the first embodiment of the present invention. FIGS. 5(A), 5(B) and 5(C) are views illustrating a state in which the ligator of the first embodiment of the present invention is inserted into a body. FIGS. 6(A) and 6(B) are views illustrating an operation for correcting a ligature-catching position with the use of the ligator of the first embodiment of the present invention. FIGS. 7(A), 7(B) and 7(C) are descriptive views illustrating a ligation operation with the use of the ligator of the first embodiment of the present invention. FIGS. 8(A), 8(B) and 8(C) are descriptive views illustrating the series of first half steps for making a half hitch of the ligature with the use of the ligator of the first embodiment of the present invention. FIGS. 9(A) and 9(B) are descriptive views illustrating the series of second half steps for making the half hitch of the ligature with the use of the ligator of the first embodiment of the present invention.

As shown in FIGS. 1 to 9, the ligator 1 of the first embodiment of the present invention comprises a ligation member 2 formed of a bar-shaped body having a constant thickness. The ligation member 2 has a front hole 3, a pair of side holes 4 and a gap portion 5. The front hole 3 has a circular shape and is formed on one end surface of the ligation member 2 by a prescribed depth in the longitudinal direction of the ligation member 2. Each of the side holes has a circular shape and they are formed on the opposite positions at one end portion of the ligation member 2 so as to be substantially at right angles to the front hole 3. The gap portion 5 is formed by cutting a prescribed portion out the one end portion of the ligation member 2, which faces the front hole 3 and the side holes 4 and extends from the inner surface to the outer surface to provide a T-shape.

In the one end portion of the ligation member 2, the partially peripheral portion, which comes into contact with the front hole 3 and extends from the one side hole 4 to the other side hole 4 is cut off. The remaining peripheral portion, which is located on the one end of the ligation member 2 so as to be adjacent to the peripheral portion cut off, is cut at a position deviating from the center between the side holes 4 by a prescribed length. Such cut-off portions form the gap portion 5. The above-mentioned remaining peripheral portion provides the pair of arcuate projections having a different length from each other. In addition, chamfering is applied to a region of from the inner surface of each of the side holes 4 to the outer surface of the ligation member 2 toward the other end of the ligation member 2 to form a recess 7 for connecting smoothly the inner surface of the side hole 4 to the outer surface of the ligation member 2. The ligation member 2 is provided at a prescribed position on the one end surface of the ligation member 2, which is in the vicinity of one of the side holes 4, with a ligature-engaging portion 2a having a recess-shape in order to facilitate an operation for making a half hitch described later.

In addition, the ligation member 2 is provided at the other end portion with a handle 10, which is to be held by an operator to facilitate to carry out a ligation operation. The handle 10 has enlarged portions that project from the outer periphery of the ligation member 2 by a prescribed length. The projecting direction of the enlarged portion of the handle 10 coincides with the position of the side holes 4 or the gap portion 5 provided on the one end portion of the ligation member 2 so that the directional posture of the one end portion of the ligation member 2 can be recognized by the direction of the enlarged portions of the handle 10. Even when the directional posture of the components of the one end portion of the ligation member 2 cannot be clearly recognized due to a small diameter of the ligation member 2 or the one end portion of the ligation member 2 cannot be recognized at all due to insertion of the one end portion into a body, the operator can recognize the directional posture of the side holes 4 and the gap portion 5 from the directional posture of the enlarged portions of the handle 10 to carry out an operation.

Now, description will be given below of a ligation operation with the use of the ligator having the above-described structure. A ligature 50 is previously put around a target part in a body, which is to be subject to a ligation operation, such as tissue in the body, a blood vessel, or the like and the opposite ends of the ligature 50 are pulled out of the body with the use of another medical appliance. An operator crosses the opposite ends of extensions of the ligature 50 to make a half hitch 51 outside the body. The opposite ends the extensions of the ligature 50, which extend from the half hitch 51, are held by a hand to lift them up so that the ligature 50 is located in the vertical direction. In such a state, the ligator 1 is placed with its one end down. The two extensions of the ligature 50 are caught by the arcuate projection 6 provided at the one end of the ligator 1 so as to be received in the gap portion 5 (see FIG. 4(A)). In such a state, the extensions of the ligature 50 can be received into the front hole 3 and the side holes 4 through the gap portion 5 (see FIG. 4(B)).

When the ligator 1 receiving the ligature 50 is moved toward the half hitch 51 while pulling the opposite ends of the extensions not so as to cause occurrence of slack of the ligature 50, contact points of the one end of the ligator 1 with the extensions of the ligature 50 shift toward the half hitch 51 with the result that the half hitch 51 is received into the front hole 3 of the ligator 1, thus providing a state in which the insertion operation into a body can be made (see FIG. 5(A)). The operator holds the extension of the ligature 50, which passes through the side hole 4 and is guided by the recess portion 7 to reach the outside of the ligator 1. Consequently, the extension of the ligature 50 cannot easily come off the side hole 4. The holding state of the end of the extension of the ligature 50 surely prevents the extension from coming off the side hole 4. The operator inserts the ligator 1 into a port 60, which is secured onto the surface of the body to serve as an opening, while holding the opposite ends of the extensions of the ligature 50 (see FIG. 5(B)).

When the operator continues to insert the ligator 1 into the body, the extensions of the ligature 50 smoothly slide on the side holes 4 and the recess portions 7, leading to shift of the half hitch 51 together with the front end of the ligator 1. In a state in which the ligator 1 is being inserted into the body, portions of the extensions of the ligature 50, which are closer to the end portion of the ligator 1 than the half hitch 51, are urged by portions of the ligator 1, having the side holes 4. This makes it possible to insert smoothly the ligator 1 into the body, while keeping the half hitch 51 in the front hole 3. Even when force having a function of moving the ligator 1 toward the outside of the body is applied to the ligator 1 due to reaction force of a valve provided in the port 60, the portions of the ligation member 2, which face the side holes 4 and the front hole 3, come into contact with the ligature 50 to support it securely, thus preventing the half hitch 51 from deviating in the port and the ligature 50 from coming off. The proper shift of the half hitch to follow securely the one end of the ligator 1 prevents an excessively large force from being applied to the ligature 50 and the target regation part in the body.

When the half hitch 51 is shifted toward the target regation part in the body, with the use of the ligator 1 and then the one end of the ligator 1 reaches the above-mentioned target part (see FIG. 5(C)), a visual inspection is made to recognize whether or not the ligature 50 is properly put around the target part in the body so that the ligation operation can be carried out. When the ligature 50 is put around the target part in the body in such an improper manner that the ligation position may deviate, the ligator 1 is moved transversely relative to the target regation part, while maintaining a state in which the ligature 50 is received in the side holes 4, to shift the ligature to the target regation part so as to return the improper state to a state in which the ligature 50 is put around the target regation part in the body in a proper manner (see FIG. 6).

When the half hitch 51 is finally shifted to the target regation part in the body (see FIG. 7(A)), the opposite ends of the ligature 50 is pulled from the outside of the body to make a knot, resulting in a ligation state of the target regation part, while keeping the ligator 1 stationary (see FIG. 7(B)). After completion of ligation operation of the target regation part in the body, the ligator 1 is held away from the target regation part (see FIG. 7(C)). Then, the ligature 50 is removed from the ligator 1 through the gap portion 5 and the ligator 1 is pulled out of the body.

An additional operation may be carried out according to demand, after the opposite ends of the ligature 50 have been pulled to make the knot, while keeping the ligator pressed against the target regation part, and then, the ligator 1 has been held away from the target regation part (see FIG. 8(A)). Such an additional operation will be described below. The ligator 1 is turned around its longitudinal axis so that one of the extensions of the ligature 50, which is received in the side hole 4 existing on the side of the shorter arcuate projection 6, comes off that side hole 4 (see FIGS. 8(B) and 8(C)). As a result, the one of extensions of the ligature 50, which has been received in the above-mentioned side hole 4, is removed from the ligator 1 through the gap portion 5 (see FIG. 9(A)). The operator manipulates the ligator 1 to move its one end, while holding the end of the extension thus removed, without slack, by a hand, so that the extension, the end of which is held by the hand, is caught by the ligature-engaging portion 2a. In such a state, the extension is pulled strongly, while keeping it received in the ligature-engaging portion 2a, so as to keep the knot in a further fastened state, thus ensuring the ligation state (see FIG. 9(B)).

In the ligator 1 of the first embodiment of the present invention, the ligation member 2 is provided at its one end portion with the front hole 3 and the side holes 4. The gap portion 5 connects the front hole 3 and the side holes 4 to the outside of the ligation member 2. In addition, the ligation member 2 is provided at its one end portion with the pair of arcuate projections 6 having different lengths from each other. The opposite ends of the extensions of the ligature 50, which has been put around the target ligation part in the body, are received in the front hole 3 and the side holes 4 through the gap portion 5. The operator carries out the insertion/ligation operation by manipulating the ligator 1 having the front hole 3, in which the half hitch is received, while holding the opposite ends of the ligature 50. Consequently, it is possible to insert the ligator 1 into the body through the port 60 without deviation of the half hitch 51 and removal of the ligature from the ligator 1, thus permitting a smooth ligation operation. In addition, the half hitch 51 can shift to follow the front end of the ligation member 2, thus preventing an excessively large force from being applied to the target ligation part in the body and the ligature 50 and improving safety. In a state in which the ligature 50 is not received in the ligator 1, it is possible to catch the ligature 50 with the arcuate projection 6 so as to receive the ligature 50 into the gap portion 5 to introduce it into the front hole 3 and the side holes 4. It is therefore possible to insert easily the ligature 50 into the front hole 3 and the side holes 4 through manipulation of the ligation member 2 within the body or outside the body. This makes it possible not only to carry out effectively an operation for inserting the ligature into the front hole and the side holes before starting a ligation operation as well as the other operation for removing the ligature from these holes after the completion of the ligation operation, but also to receive the ligature into the respective holes formed on the front end portion of the ligation member or remove it therefrom in a desired manner during a knot operation in the body, so as to make easily and appropriately an elaborate and ingenious operation, thus improving remarkably the operation efficiency in the body and reducing an operational burden of the operator. The ligation member is provided with a portion to be inserted into the body, which has a cylindrical shape. As a result, it is possible to make an opening of the port 60 smaller and decrease a gap between the port 60 and the ligation member 2, thus permitting to reduce a gas leakage ratio upon operation according to aeroperitoneum.

In the ligator 1 of the first embodiment of the present invention, a cut portion of the one end portion of the ligation member 2, which forms the vertical portion of the T-shaped gap portion 5, is displaced to the one side hole 4 so that the pair of arcuate projections 6 have the different length from each other. The ligator of the present invention is not limited only to such a structure. The vertical portion of the T-shaped gap portion 5 may be placed just in the middle between the pair of side holes 4 to provide a symmetrical shape so that the pair of arcuate projections 6 have the same length. In such a structure, it is possible to prevent effectively the ligature 50 from coming off the gap portion 5. Accordingly, the ligature 50 does not come off the front end of the ligator 2 during the ligation operation, unless the ligature 50 held by the operator is loosened. The ligation member 2 may be provided only with the front hole 3 and the side holes 4 without the gap portion 5. In such a structure, it is possible to prevent completely the ligature from being removed from the ligator 1, permitting to shift securely the half hitch 51 to the target ligation part in the body to carry out the ligation operation.

Figure 11A:
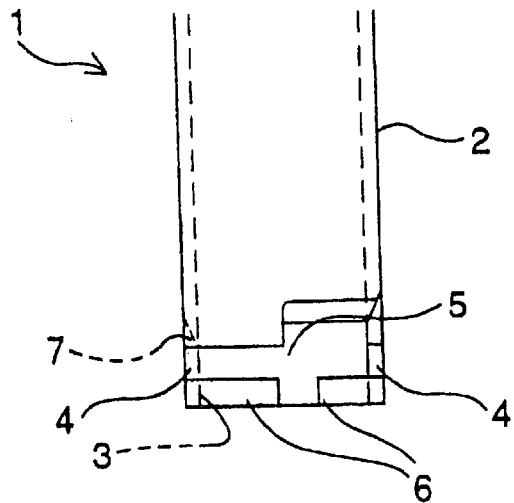
FIGS. 11(A), 11(B) and 11(C) are a partial front view, a bottom view and a partial side view illustrating the other modified ligator of the first embodiment of the present invention, respectively.
Figure 11B:
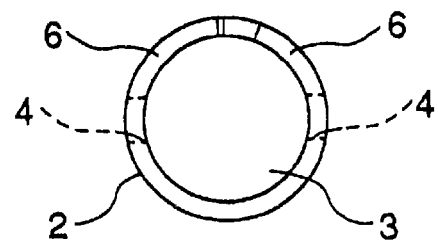
Figure 11C:
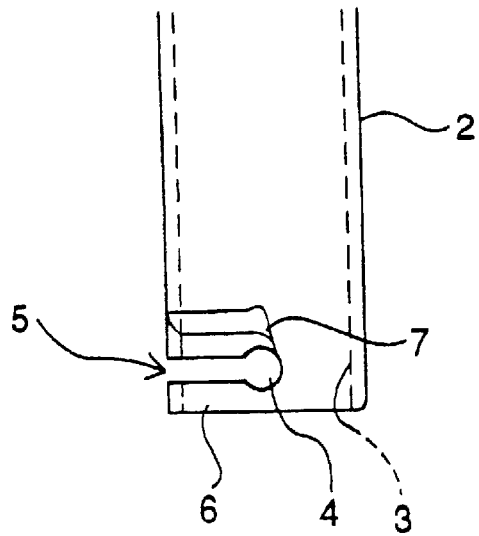

In the ligator 1 of the first embodiment of the present invention, the ligation member 2 is provided with the T-shaped gap portion, through which the ligature 50 can be received into the front hole 3 and the side holes 4. A cutting-off working may be applied to the end surface of the ligation member 2 over a prescribed region, which faces the one arcuate projection 6 (i.e., the right-hand side projection 6 in FIG. 11(A)) through the gap portion 5, and then the edge portion of the ligation member 2 formed by such a cutting-off working is chamfered on the outer surface side, thus providing the gap portion 5 partially enlarged. Such an enlarged gap portion 5 facilitates carrying out the operation for removing one of the extensions of the ligature 50 received in the side hole 4 therefrom when an operation for keeping the knot in a further fastened state after completion of the knot-making operation, thus improving operational efficiency.

Second Embodiment of the Present Invention

Figure 13A:
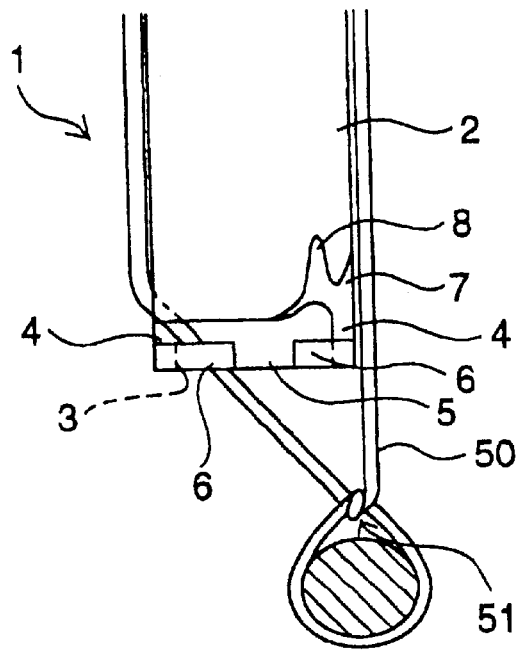
FIGS. 13(A) and 13(B) are descriptive views illustrating the series of first half steps for carrying out a ligature-insertion operation in a body with the use of the ligator of the second embodiment of the present invention.
Figure 13B:
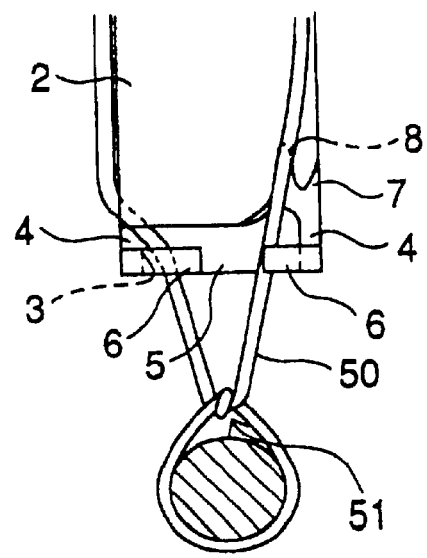
Figure 14A:
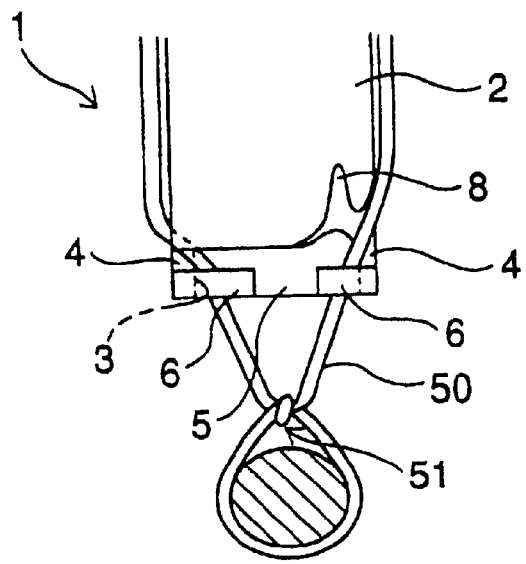
FIGS. 14(A) and 14(B) are descriptive views illustrating the series of second half steps for carrying out the ligature-insertion operation in the body with the use of the ligator of the second embodiment of the present invention.
Figure 14B:
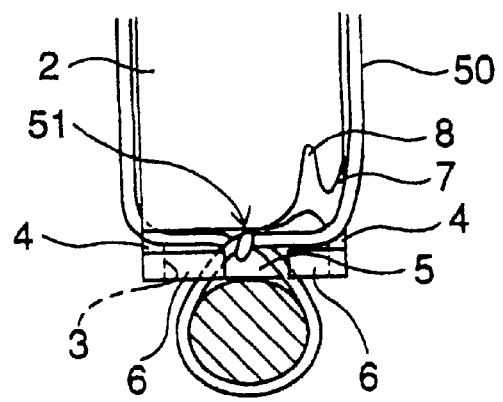

Now, the ligator of the second embodiment of the present invention will be described with reference to FIGS. 12 to 14. FIGS. 12(A), 12(B) and 12(C) are a partial front view, a bottom view and a partial side view illustrating the ligator of the second embodiment of the present invention, respectively. FIGS. 13(A) and 13(B) are descriptive views illustrating the series of first half steps for carrying out a ligature-insertion operation in a body with the use of the ligator of the second embodiment of the present invention. FIGS. 14(A) and 14(B) are descriptive views illustrating the series of second half steps for carrying out the ligature-insertion operation in the body with the use of the ligator of the second embodiment of the present invention.

Figure 12A:
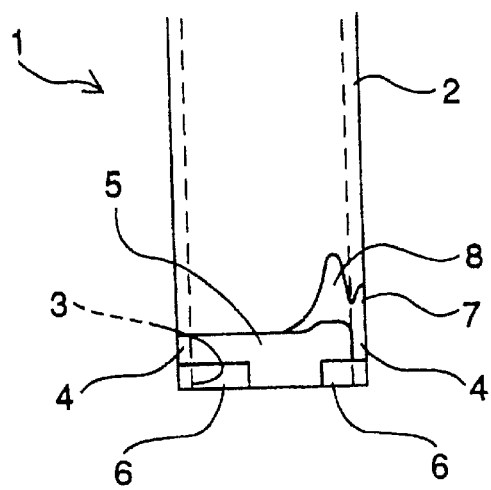
FIGS. 12(A), 12(B) and 12(C) are a partial front view, a bottom view and a partial side view illustrating the ligator of the second embodiment of the present invention, respectively.
Figure 12B:
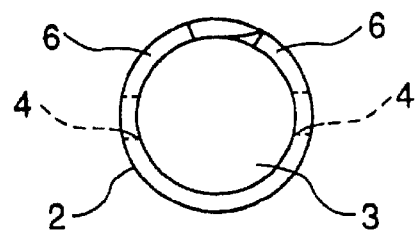
Figure 12C:
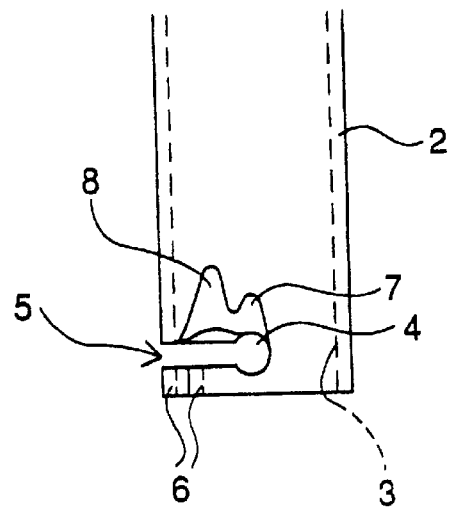

As shown in FIGS. 12 to 14, the ligator 1 of the second embodiment of the present invention comprises the ligation member 2, which has the front hole 3, the side holes 4 and the gap portion 5 in the same manner as in the first embodiment. With respect to different features from the first embodiment, the ligation member 2 has another recess portion 8. The recess portion 8 is formed by chamfering the portion from the end surface of the ligation member 2 at a prescribed region, which faces the front end of the one arcuate projection 6 (i.e., the right-hand side projection 6 in FIG. 12(A)) through the gap portion 5, to the outer surface of the ligation member toward the other end (i.e., the upper end in FIG. 12(A)) thereof. The recess portion 8 smoothly connects the above-mentioned end surface of the ligation member 2 with the outer surface thereof in this manner.

Now, description will be given below of a ligation operation with the use of the ligator having the above-described structure. A ligature 50 is previously put around the target ligation part in the body and the opposite ends of the ligature 50 are pulled out of the body with the use of another medical appliance in the same manner as the first embodiment. An operator crosses the opposite ends of extensions of the ligature 50 to make a half hitch 51 outside the body. The opposite ends of the extensions of the ligature 50, which extend from the half hitch 51, are held by a hand and the ligator 1 is manipulated. The two extensions of the ligature 50 are caught by the arcuate projection 6 so as to be received in the gap portion 5. In such a state, the extensions of the ligature 50 can be received into the front hole 3 and the side holes 4 through the gap portion 5. Then, the half hitch 51 of the ligature 50 is received into the front hole 3 of the ligator 1. The operator inserts the ligator 1 into the body through a port 60, while holding the opposite ends of the extensions of the ligature 50 so that the half hitch 51 enters the body together with the front end of the ligator 1.

Even when the ligature 50 is removed from the gap portion 5 in the body during an operation in which the ligator 1 approaches the target ligation part in the body (see FIG. 13(A)), it is possible to catch easily the ligature 50 with the arcuate projection 6 to receive it into the gap portion 5 (see FIG. 13(A)) by manipulating the ligator 1 by the operator so as to place the ligature 50 in the recess portion 8 (see FIG. 13(B)), returning to a state in which the ligature 50 is received in the front hole 3 and the side holes 4 (see FIG. 14(B)). There is required no operation for pulling the ligator 1 out of the body and then inserting the ligature 50 into these holes.

When the one end of the ligator 1 reaches the target ligation part in the body, the operator pulls the opposite ends of the extensions of the ligature 50 from the outside to make a knot, while pressing the ligator 1 against the target ligation part in the body. Even when the ligature 1 held by the operator is advertently loosened during such a knot-making operation so that the ligature 50 is removed from the one end of the ligator 1, the manipulation of the ligator 1 carried out so as to place the removed ligature 50 into the recess portion 8 in the same manner as described above makes it possible to introduce the ligature 50 into the side hole 4, permitting to a secured ligation operation. After making the knot and then keeping the knot in a further fastened state in the same manner as the first embodiment, it is possible to place the removed extension of the ligature 50 in the recess portion 8 to receive it in the gap potion 5 so as to return the extension into the side hole 4, thus permitting to a further fastening operation.

In the ligator 1 of the second embodiment of the present invention, the ligation member is provided with the recess portion 8 smoothly connecting the end surface of the ligation member 2 at a prescribed region, which faces the front end of the one arcuate projection 6 (i.e., the right-hand side projection 6 in FIG. 12(A)) through the gap portion 5, to the outer surface of the ligation member. When the ligature 50 is brought into contact with the ligation member 2 so as to be placed along the recess portion 8, force having a function of pulling the ligature 50 into the front hole 3 is applied to the ligature 50, providing a state in which the ligature 50 can easily be caught by the arcuate projection 6. Even when the ligature 50 comes off the gap portion 50 so as to be away from the ligation member 2 in the body, the ligature 50 can easily be caught by the arcuate projection 6 to lead the ligature 50 into the gap portion 5 through operation of the operator, so as to return a proper state in which the ligature 50 is received in the front hole 3 and the side holes 4. It is therefore possible to carry out consecutively an operation for knotting the ligature 50 in the body in an appropriate manner when the ligator is once inserted into the body. As a result, the ligation operation can be carried out in a short period of time, thus remarkably reducing an operational burden of the operator.

Third Embodiment of the Present Invention

Figure 15A:
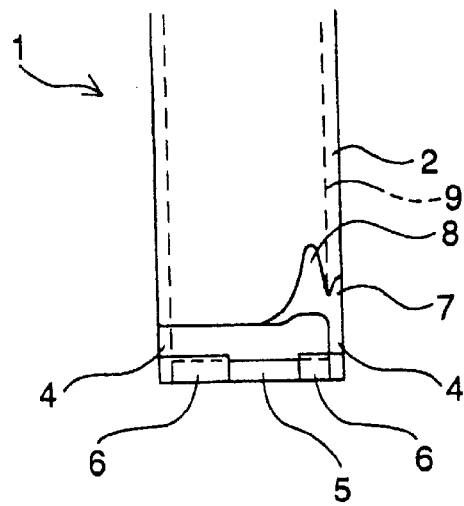
FIGS. 15(A), 15(B) and 15(C) are a partial front view, a bottom view and a partial side view illustrating the ligator of the third embodiment of the present invention, respectively.
Figure 15B:
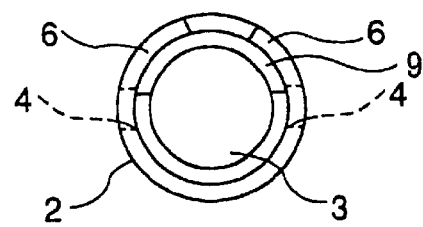
Figure 15C:
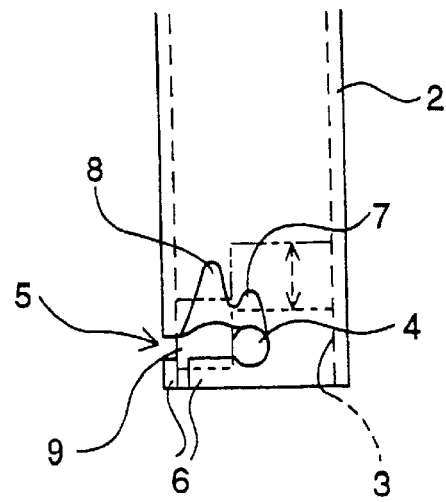

Now, the ligator of the third embodiment of the present invention will be described with reference to FIGS. 15(A) to 15(C). FIGS. 15(A), 15(B) and 15(C) are a partial front view, a bottom view and a partial side view illustrating the ligator of the third embodiment of the present invention, respectively.

As shown in FIGS. 15(A) to 15(C), the ligator 1 of the third embodiment of the present invention comprises the ligation member 2, which has the front hole 3, the side holes 4, the gap portion 5 and the recess portion 8 in the same manner as in the second embodiment. With respect to different features from the second embodiment, the front hole 3 passes through the ligation member 2 in its longitudinal direction and an inner tube 9 is slidably placed in the front hole 3.

The inner tube 9 is formed of a tubular member, which is placed detachably into the front hole 3. The inner tube 9 is provided at its front end with a stepped portion. The inner tube 9 is slidably placed into the front hole 3 in the longitudinal direction of the ligation member 2 between the first position in which the front end of the inner tube 9 is placed beyond the gap portion 5 to reach the other end of the ligation member 2 and the second position in which the tubular member closes an opening between the both side holes 4 of the gap portion 5 from the side of the front hole 3. An operator can control the movement of the inner tube 9 relative to the ligation member 2 from the other end side thereof. The ligation member 2 may be provided in its inside with a device for applying force having a function of moving the inner tube 9 toward the other end of the ligation member 2 to the inner tube 9. According to such a structure, the operator urges, from the other end side of the ligation member, the inner tube 9 against the above-mentioned force-applying device toward the one end of the ligation member 2 to provide a closed state of the gap portion 5. Removal of pressure from the inner tube 9 causes the inner tube 9 to move by the function of the force-applying device to provide an opened state of the gap portion 5. The operator can easily carry out an opening or closing operation of the gap portion 5 by a single hand in this manner.

Now, description will be given below of a ligation operation with the use of the ligator having the above-described structure. A ligature 50 is previously put around the target ligation part in the body and the opposite ends of the ligature 50 are pulled out of the body with the use of another medical appliance in the same manner as the second embodiment. When the ligator 1 is manipulated in a state in which the inner tube 9 moves to open the gap portion 5, and the pair of extensions of the ligature 50 are brought into contact with the ligation member 2 so as to be placed along the recess portion 8, force having a function of pulling the ligature 50 into the front hole 3 is applied to the ligature 50, providing a state in which the ligature 50 can easily be caught by the arcuate projection 6. In this state, when the pair of extensions of the ligature 50 are caught by the arcuate projection 6 to be received into the gap portion 5, the extensions of the ligature 50 is received into the front hole 3 and the side holes 4 through the gap portion 5.

After the extensions are received in the side holes 4, the operator moves the inner tube 9 toward the one end of the ligator 1 to close the opening between the both side holes 4 of the gap portion 5 from the side of the front hole 3 by means of the front end of the inner tube 9. A partially closed condition of the gap portion 5 can maintain a state in which the ligature 50 cannot be removed from the side holes 4. Then, the half hitch 51 of the ligature 50 is received into the front hole 3 of the ligator 1 in the same manner as the second embodiment. The operator inserts the ligator 1 into the body through a port 60, while holding the opposite ends of the extensions of the ligature 50 so that the half hitch 51 enters the body together with the front end of the ligator 1.

When the one end of the ligator 1 reaches the target ligation part in the body, the operator pulls the opposite ends of the extensions of the ligature 50 from the outside to make a knot, while pressing the ligator 1 against the target ligation part in the body. After making the knot, the inner tube 9 received in the ligation member 2 is moved toward the other end of the ligator 1 to maintain an opened state of the gap portion 5. Then, the extensions of the ligature 50 can be removed from the one end of the ligator 1. Additional operation to keep the knot in a further fastened state may be carried out in the same manner as the first embodiment.

In the ligator of the third embodiment of the present invention, the inner tube 9 is provided in the front hole 3 so as to be slidable in the longitudinal direction of the ligation member 2 within a prescribed range. As a result, there can be selected any one of modes, i.e., one mode in which the inner tube 9 is moved to open the gap portion 5 through operation of the operator so that the ligature-insertion or removal operation is permitted through the gap portion 5, and the other mode in which the inner tube 9 is moved to close partially the gap portion 5 so that any ligature-insertion or removal operation is not permitted. It is therefore possible to control the ligature 50 to come in or out of the ligation member 2 through the gap portion 5. This makes it possible to insert the ligator 1 into the body and cause it to approach the target ligation part in the body, while preventing completely the ligature 50 from coming off the gap portion 5. Accordingly, efficiency of an insertion operation of the ligator 1 into the body can be remarkably improved, while maintaining an easy operation for inserting the ligature 50 into the front hole 3 and the side holes 4, thus remarkably reducing an operational burden of the operator.

Fourth Embodiment of the Present Invention

Figure 16A:
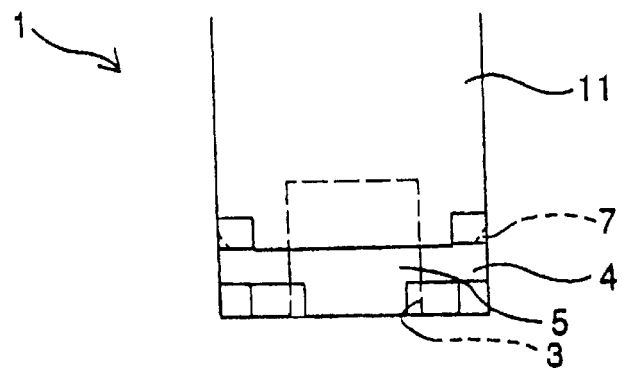
FIGS. 16(A), 16(B) and 16(C) are a partial front view, a bottom view and a partial side view illustrating the ligator of the fourth embodiment of the present invention, respectively.
Figure 16B:
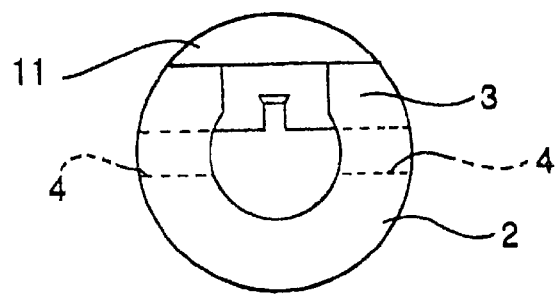
Figure 16C:
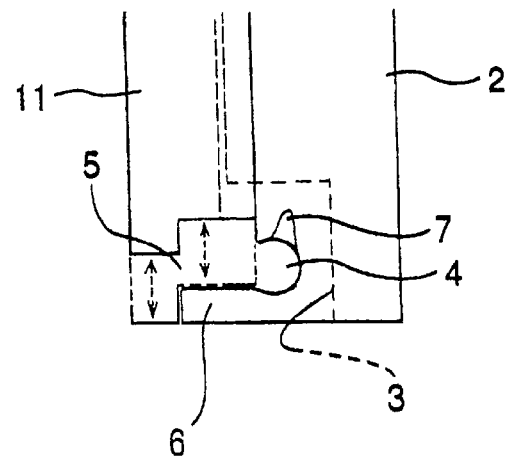

Now, the ligator of the fourth embodiment of the present invention will be described with reference to FIGS. 16(A) to 16(C). FIGS. 16(A), 16(B) and 16(C) are a partial front view, a bottom view and a partial side view illustrating the ligator of the fourth embodiment of the present invention, respectively.

As shown in FIGS. 16(A) to 16(C), the ligator 1 of the fourth embodiment of the present invention comprises the ligation member 2, which has the front hole 3, the side holes 4 and the gap portion 5 in the same manner as in the first embodiment. With respect to different features from the first embodiment, an opening or closing member 11 is slidably provided in the ligation member 2 to open or close the gap portion 5.

The opening or closing member 11 is formed into a semi-cylindrical shape, which is combined with the ligation member 2 to provide a cylindrical shape. The opening or closing member 11 is provided at its front end with a stepped portion. The opening or closing member 11 is slidably placed in the ligation member 2 in the longitudinal direction thereof between the first position in which the front end of the opening or closing member 11 is separated from the arcuate projections 6 provided at the one end of the ligation member 2 to provide an opened state of the gap portion 5 and the second position in which the opening or closing member 11 is fitted into the gap portion 5 to provide a closed state of the gap portion 5. An operator can control the movement of the opening or closing member 11 relative to the ligation member 2 from the other end side thereof. There may be provided between the ligation member 2 and the opening or closing member 11 a device for applying force having a function of moving the opening or closing member 11 toward the other end of the ligation member 2 to the opening or closing member 11. According to such a structure, the operator urges, from the other end side of the ligation member, the opening or closing member 11 against the above-mentioned force-applying device toward the one end of the ligation member 2 to provide a closed state of the gap portion 5. Removal of pressure from the opening or closing member 11 causes the opening or closing member 11 to move by the function of the force-applying device to provide an opened state of the gap portion 5. The operator can easily carry out an opening or closing operation of the gap portion 5 by a single hand in this manner.

Now, description will be given below of a ligation operation with the use of the ligator having the above-described structure. A ligature 50 is previously put around the target ligation part in the body and the opposite ends of the ligature 50 are pulled out of the body with the use of another medical appliance in the same manner as the first embodiment. When the ligator 1 is manipulated in a state in which the opening or closing member 11 moves to open the gap portion 5 so that the pair of extensions of the ligature 50 are caught by the arcuate projection 6 to be received into the gap portion 5, the extensions of the ligature 50 is received into the front hole 3 and the side holes 4 through the gap portion 5.

After the extensions are received in the side holes 4, the operator moves the opening or closing member 11 toward the one end of the ligator 1 to close the gap portion 5 by means of the front end of the opening or closing member 11. A closed condition of the gap portion 5 can maintain a state in which the ligature 50 cannot be removed from the side holes 4. Then, the half hitch 51 of the ligature 50 is received into the front hole 3 of the ligator 1 in the same manner as the first embodiment. The operator inserts the ligator 1 into the body through a port 60, while holding the opposite ends of the extensions of the ligature 50 so that the half hitch 51 enters the body together with the front end of the ligator 1.

When the one end of the ligator 1 reaches the target ligation part in the body, the operator pulls the opposite ends of the extensions of the ligature 50 from the outside to make a knot, while pressing the ligator 1 against the target ligation part in the body. After making the knot, the opening or closing member 11 received in the ligation member 2 is moved toward the other end of the ligator 1 to maintain an opened state of the gap portion 5. Then, the extensions of the ligature 50 can be removed from the one end of the ligator 1. Additional operation to keep the knot in a further fastened state may be carried out in the same manner as the first embodiment.

In the ligator of the fourth embodiment of the present invention, the opening or closing member 11 is mounted movably on the ligation member 2 so that there can be selected any one of modes, i.e., one mode in which the opening or closing member 11 is moved to open the gap portion 5 through operation of the operator so that the ligature-insertion or removal operation is permitted through the gap portion 5, and the other mode in which the opening or closing member 11 is moved to close the gap portion 5 so that any ligature-insertion or removal operation is not permitted. It is therefore possible to insert the ligator into the body and cause it to approach the target ligation part in the body, while preventing completely the ligature 50 from coming off the gap portion 5. Accordingly, efficiency of an insertion operation of the ligator 1 into the body can be remarkably improved, while maintaining an easy operation for inserting the ligature 50 into the front hole 3 and the side holes 4, thus remarkably reducing an operational burden of the operator.

Figure 17:
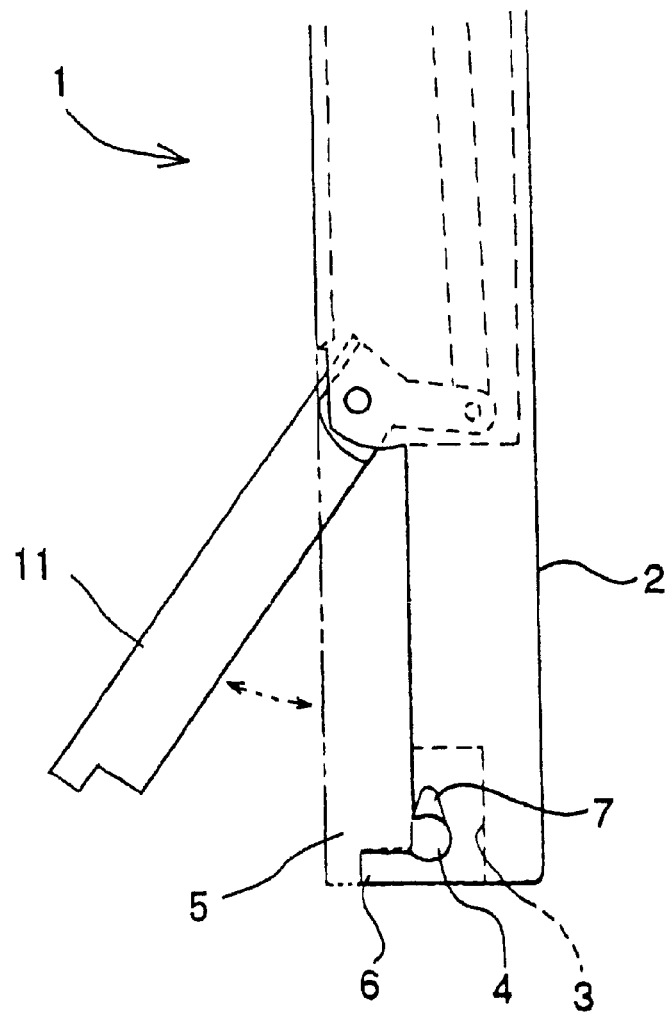
FIG. 17 is a partial side view illustrating the modified ligator of the fourth embodiment of the present invention.
Figure 18A:
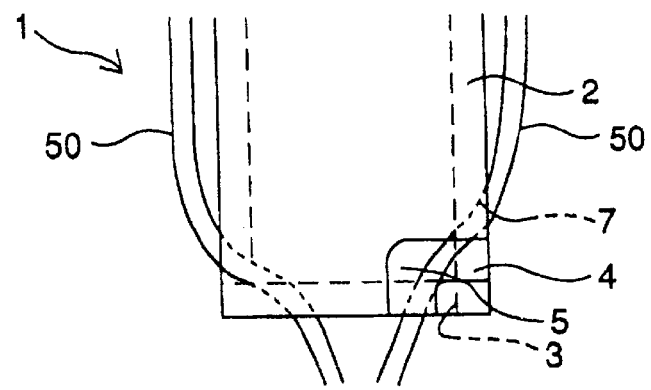
FIGS. 18(A), 18(B) and 18(C) are a partial front view, a bottom view and a partial side view illustrating the ligator of another embodiment of the present invention, respectively.
Figure 18B:
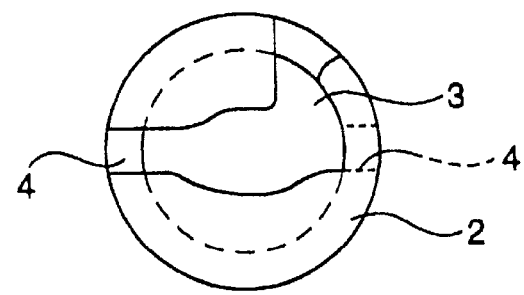
Figure 18C:
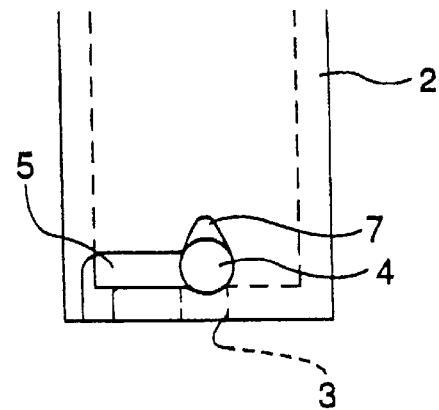

In the forth embodiment of the present invention, the opening or closing member 11 slides relative to the ligation member 2 to open or close the gap portion 5. The present invention is not limited only to such structure. The opening or closing member 11 may be pivoted on a prescribed position of the ligation member so as to be swingable relative to the ligation member 2 as shown in FIG. 17. In such a case, the opening or closing member 11 can be moved to open or close the gap portion 5 through a remote control from the other end side of the ligation member 2. According to such a structure, there can be selected, as an occasion demands, any one of modes, i.e., one mode in which the ligature-insertion or removal operation is permitted through the gap portion 5, and the other mode in which any ligature-insertion or removal operation is not permitted, thus improving an operational efficiency with the use of the ligator 1. In addition, it is possible to hold the ligature 50 or the like between the opening or closing member 11 and the ligation member 2 in the same manner as the conventional pair of forceps, thus fitting for various purposes.

Figure 19A:
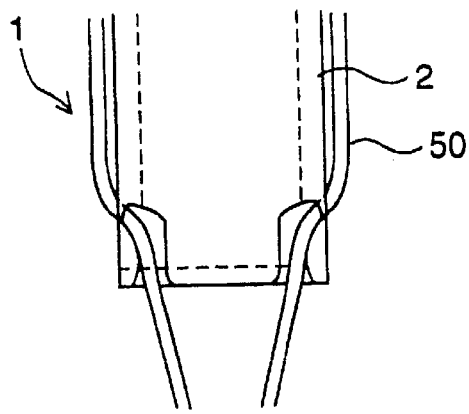
FIGS. 19(A), 19(B) and 19(C) are a partial front view, a bottom view and a partial side view illustrating the ligator of further another embodiment of the present invention, respectively.
Figure 19B:
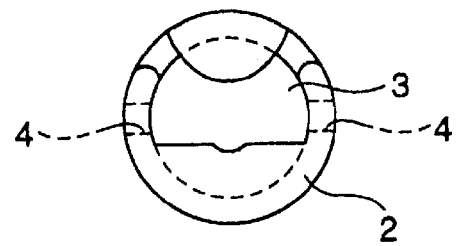
Figure 19C:
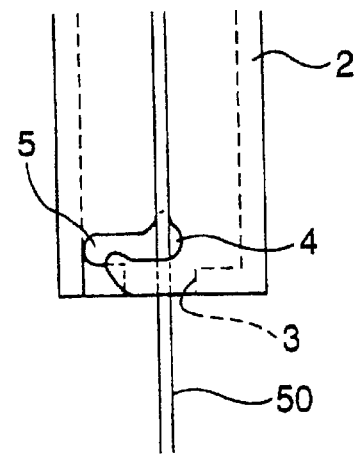
Figure 20A:
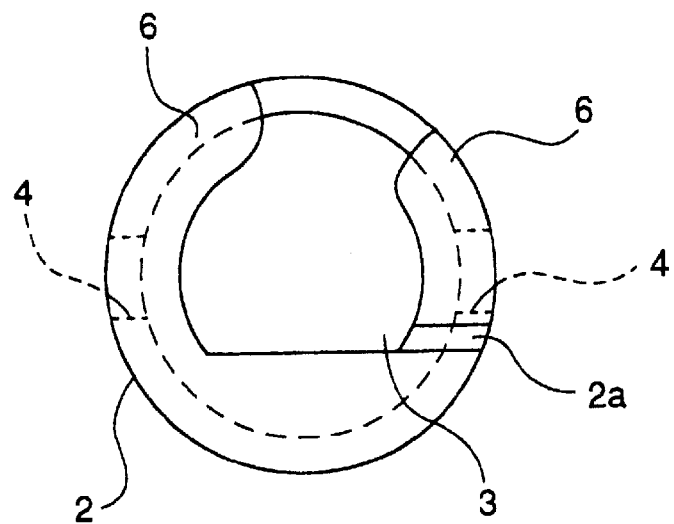
FIGS. 20(A) and 20(B) are a bottom view and a partial side view illustrating the ligator of still further another embodiment of the present invention, respectively.
Figure 20B:
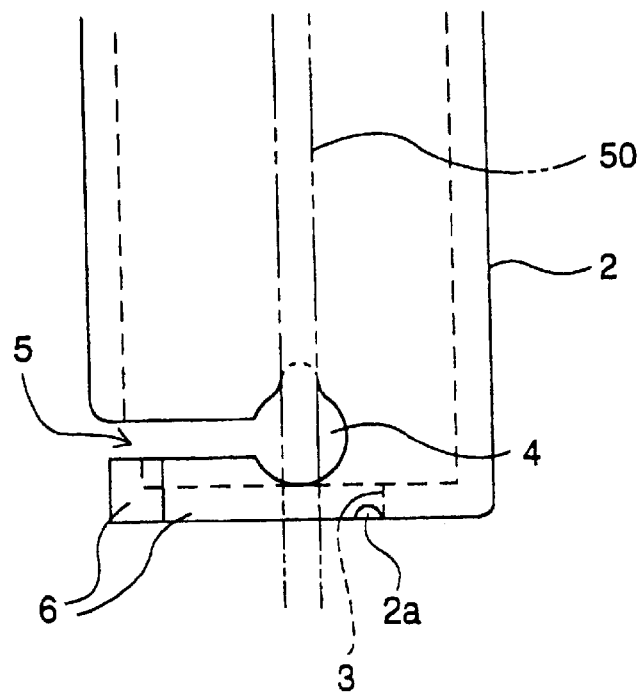
Figure 21:
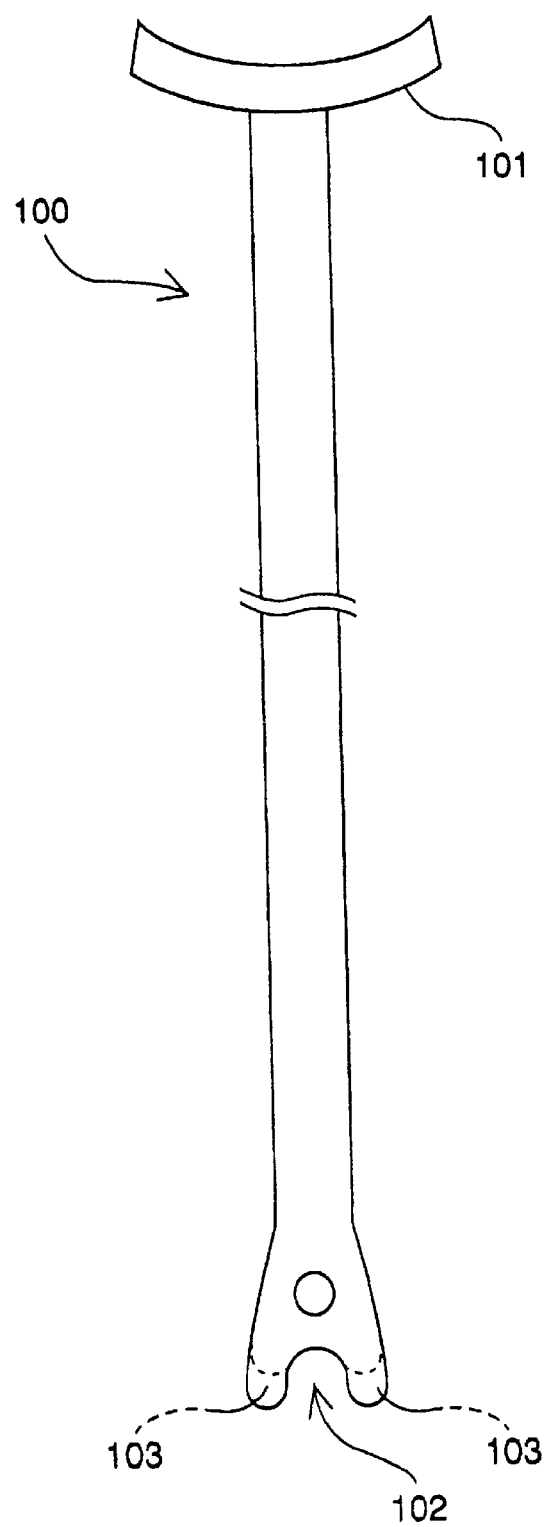
FIG. 21 is a schematic structural view illustrating the conventional ligator.
Figure 22:
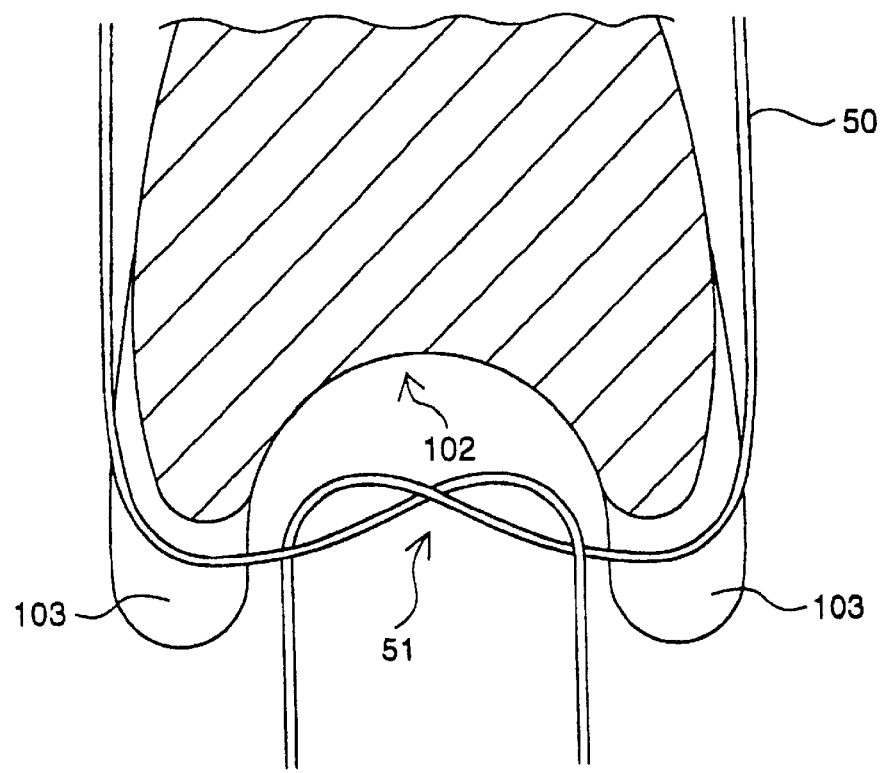
FIG. 22 is a partial vertical cross-sectional view illustrating the conventional ligator.

In the above-described first to third embodiments of the present invention, the ligation member 2 has at its front end the front hole 3, which is formed so as to occupy the major area on the front-end surface. The present invention is not limited only to such a feature. The occupied area of the front hole 3 may be made smaller to provide the front surface having a sufficient area to ensure a prescribed contact area with tissue in the body. With respect to the ligator, there is a strong demand for a smaller-diameter ligator in order to make an incision portion excessively smaller on the body surface in endoscopic surgery, reducing a burden of a person to be operated. Simple small-diameter structure of a ligator may cause it to easily stick into tissue in the body when the ligator comes into contact with the tissue. In view of this fact, the above-mentioned feature can provide the small-diameter ligator and secure a prescribed area of the front surface of it, thus ensuring safety upon contact of the ligator with the tissue. The ligator may have the shape of the front-end portion as shown in FIGS. 19(A), 19(B) and 19(C) taking into consideration the area of the front-end surface of the ligator and an easy operation for inserting the ligature 50 into the front hole 3 and the side holes 4 through the gap portion 5. The ligator may have the shape as shown in FIG. 20, in which the easy entire operation including a ligature-insertion operation and a ligation operation can be ensured in the same manner as the first embodiment and increase in area of the front surface of the ligator and improved safety can be achieved.

In the ligator of the first to third embodiments of the present invention, the ligation member 2 is formed of a bar-shaped body having a constant thickness and the front hole 3 is formed on the front end of the ligation member 2. The present invention is not limited only to such a feature. The ligation member 2 may be formed of a hollow cylindrical body, the inner space of which can be used as the front hole 3. According to such a feature, the easy entire operation including a ligature-insertion operation and a ligation operation can be ensured, simplifying the structure of the ligator and leading to an easy manufacture and a low manufacturing cost.

According to the present invention as described in detail, the bar-shaped ligation member is provided on its front end with the front hole and the side holes. An operator passes the opposite ends extending from a half hitch of a ligature through the front hole and the side holes so that the half hitch is placed within the front hole. The operator carries out a ligation operation while holding the opposite ends of the ligature. When the ligator is inserted into a body, the side holes urge the ligature to shift the half hitch of the ligature into the body, while keeping the half hitch within the front hole of the ligator. When the ligator is pulled out of the body, the ligature comes into contact with the ligation member within the front hole and the side holes to hold securely the ligature. It is therefore possible to pass the ligator through a port to carry out the ligation operation without causing deviation of the half hitch and slip-off of the ligature. In addition, the half hitch of the ligature shifts together with the front end of the ligator to prevent an excessively large force from being applied to the target part, which is to be subject to the ligation operation, thus improving safety. The ligation member is provided with a portion to be inserted into the body, which has a shape with substantially the constant thickness in the longitudinal direction of the ligation member. As a result, it is possible to make an opening of the port smaller, thus permitting to reduce a gas leakage ratio upon operation according to aeroperitoneum.

According to the other feature of the present invention, the ligation member is provided with the recesses for connecting partially the outer surface of the ligation member and the inner surface of the side holes. A ligature received in the side hole is guided into the recess to reach the outside of the ligator, thus preventing the ligature from coming easily off the recess to secure a proper receiving state of the ligature within the side hole. The ligature does not come off the front end of the ligator so long as an operator holds the opposite ends of the ligature. In addition, when the ligator is inserted into a body, the ligature can smoothly move through the side hole toward the outside of the ligator, thus reducing contact resistance of the ligature with the ligation member. Accordingly, it is possible to carry out an insertion operation of the ligator in the body without causing slack of the ligature.

According to the other feature of the present invention, the ligation member is provided at its one end portion with the gap portion through which the front hole and the side holes communicates with each other and these holes also communicate with the outside. Accordingly, it is possible to insert the ligature into the front hole and the side holes through the gap portion and to remove the ligature from these holes through the gap portion. It is therefore possible to carry out effectively an operation for inserting the ligature into the front hole and the side holes before starting a ligation operation as well as the other operation for removing the ligature from these holes after the completion of the ligation operation. As a result, a period of time required for the ligation operation can be reduced, and a burden of both the operator and a person to be operated can also be reduced.

According to the other feature of the present invention, the ligation member is formed into the hollow cylindrical shape in at least prescribed region so that the front hole is formed as a cylindrical space and the cross-section of the portion to be inserted into a body through the conventional port provides a symmetric shape. This makes it possible to reduce the gap between the port and the ligation member, thus permitting to reduce remarkably a gas leakage ratio upon operation according to aeroperitoneum and simplifying the structure of the ligator and leading to an easy manufacture and a low manufacturing cost.

According to the other feature of the present invention, the gap portion extends from the one side hole to the other side hole and further extends from the middle between the side holes to the one end surface of the ligation member so as to form a T-shape. As a result, the ligation member is provided on its one end portion with a pair of projections, which are defined by the gap portion, the front hole and the side holes. An operator can have the ligature caught by one or both of the projections before carrying out a ligature-insertion operation to obtain a state in which the ligature can be received in the front hole and the side holes. It is therefore possible to facilitate to pass the ligature through the front hole and the side holes by handling of the ligator. It is therefore possible not only to carry out effectively an operation for inserting the ligature into the front hole and the side holes before starting a ligation operation as well as the other operation for removing the ligature from these holes after the completion of the ligation operation, but also to receive the ligature into the respective holes formed on the front end portion of the ligation member or remove it therefrom in a desired manner during a knot operation in the body, so as to make easily and appropriately an elaborate and ingenious operation, thus improving remarkably the operation efficiency in the body.

According to the other feature of the present invention, the inner tube is provided in the front hole so as to be slidable in the longitudinal direction of the ligation member within a prescribed range. As a result, there can be selected any one of modes, i.e., one mode in which the inner tube is moved to open the gap portion through operation of the operator so that the ligature-insertion or removal operation is permitted through the gap portion, and the other mode in which the inner tube is moved to close partially the gap portion so that any ligature-insertion or removal operation is not permitted. It is therefore possible to control the ligature to come in or out of the ligation member through the gap portion. This makes it possible to insert the ligator into the body and cause it to approach a target part in the body, to which is to be subject to a ligation operation, while preventing completely the ligature from coming off the gap portion. Accordingly, efficiency of an insertion operation of the ligator into the body can be remarkably improved, while maintaining an easy operation for inserting the ligature into the front hole and the side holes, thus remarkably reducing an operational burden of the operator.

According to the other feature of the present invention, there is provided the other recess connecting partially the prescribed portion of the end surface of said ligation member facing said gap portion and the outer surface of said ligation member. When the ligature is brought into contact with the ligation member so as to be placed along the other recess portion, force having a function of pulling the ligature into the front hole is applied to the ligature, providing a state in which the ligature can easily be caught by the projection. Even when the ligature comes off the gap portion of the ligation member so as to be away from the ligation member in the body, the ligature can easily be caught by the projection to lead the ligature into the gap portion through operation of the operator, so as to return a proper state in which the ligature is received in the front hole and the side holes. It is therefore possible to carry out consecutively an operation for knotting the ligature in the body in an appropriate manner when the ligator is once inserted into the body. There is required no operation for inserting the ligator into the body and removing it therefrom several times to receive the ligature in the front hole and the side holes, permitting to smooth progress of the ligation operation without taking much time, thus remarkably reducing an operational burden of the operator.

According to the other feature of the present invention, the opening or closing member is mounted movably on the ligation member so that there can be selected any one of modes, i.e., one mode in which the opening or closing member is moved to open the gap portion through operation of the operator so that the ligature-insertion or removal operation is permitted through the gap portion, and the other mode in which the opening or closing member is moved to close the gap portion so that any ligature-insertion or removal operation is not permitted. It is therefore possible to insert the ligator into the body and cause it to approach a target part in the body, to which is to be subject to a ligation operation, while preventing completely the ligature from coming off the gap portion. Accordingly, efficiency of an insertion operation of the ligator into the body can be remarkably improved, while maintaining an easy operation for inserting the ligature into the front hole and the side holes, thus remarkably reducing an operational burden of the operator.

What is claimed is:

1. A ligator comprising:

a ligation member formed of a bar-shaped body having a constant thickness in a region extending by at least a prescribed length from one end of said ligation member;

a front hole formed on one end surface of said ligation member, said front hole having a prescribed shape and a prescribed depth in a longitudinal direction of said ligation member; and a pair of side holes formed on opposite positions at one end portion of said ligation member so as to be substantially at right angles to said front hole, said front hole being located between said opposite positions, and said side holes communicating with said front hole, opposite ends of a ligature to be knotted passing through said front hole and said side holes.

2. The ligator as claimed in claim 1, wherein:

said ligation member is provided with a pair of recesses each connecting smoothly an inner surface of each of said side holes of said ligation member and an outer surface of said ligation member, each of said recesses being formed by chamfering an edge portion from said inner surface to said outer surface toward an other end of said ligation member.

3. The ligator as claimed in claim 2, wherein:

said ligation member is provided with a gap portion, which causes said front hole to communicates with said side holes, said gap portion being formed by cutting a prescribed portion out of said ligation member, which faces said front hole and said side holes formed at the one end portion of said ligation member and extends from the inner surface to the outer surface, said gap portion permitting said ligature to be received in said front hole and said side holes or removed therefrom.

4. The ligator as claimed in claim 3, wherein:

said ligation member is formed into a cylindrical shape having a hollow portion in said region extending by said at least a prescribed length, said hollow portion forming said front hole.

5. The ligator as claimed in claim 1, wherein:

said ligation member is provided with a gap portion, which causes said front hole to communicates with said side holes, said gap portion being formed by cutting a prescribed portion out of said ligation member, which faces said front hole and said side holes formed at the one end portion of said ligation member and extends from the inner surface to the outer surface, said gap portion permitting said ligature to be received in said front hole and said side holes or removed therefrom.

6. The ligator as claimed in claim 5, wherein:

said ligation member is formed into a cylindrical shape having a hollow portion in said region extending by said at least a prescribed length, said hollow portion forming said front hole.

7. A ligator comprising:

a ligation member formed of a bar-shaped body having a constant thickness in a region extending by at least a prescribed length from one end of said ligation member;

a front hole formed on one end surface of said ligation member, said front hole having a prescribed shape and a prescribed depth in a longitudinal direction of said ligation member;

a pair of side holes formed on opposite positions at one end portion of said ligation member so as to be substantially at right angles to said front hole, said front hole being located between said opposite positions, and said side holes communicating with said front hole, opposite ends of a ligature to be knotted passing through said front hole and said side holes, wherein:

said ligation member is provided with a gap portion, which causes said front hole to communicate with said side holes, said gap portion being formed by cutting a prescribed portion out of said ligation member, which faces said front hole and said side holes formed at the one end portion said ligation member and extends from the inner surface to the outer surface, said gap portion permitting said ligature to be received in said front hole and said side holes or removed therefrom, wherein said ligation member is formed into a cylindrical shape having a hollow portion in said region extended by said at least prescribed length, said hollow portion forming said front hole, and wherein:

said gap portion is formed by cutting partially out of a peripheral portion of said ligation member, which cones into contact with said front hole and extends from one of said side holes to an other of said side holes, and then removing at least a part of an end peripheral portion of said ligation member, which is placed along said peripheral portion thus out, thereby said end peripheral portion forming a pair of arcuate projections.

8. The ligator as claimed in claim 7, wherein:

said front hole extends beyond a position of each of said side holes by a prescribed length toward the other end side of said ligation member; and said ligator further comprises an inner tube, which is formed of a tubular member having a prescribed cross-section, which can be inserted into said front hole, said inner tube being slidably received in said front hole in the longitudinal direction of said ligation member from a position in which a front end of said tubular member is placed beyond said gap portion to reach the other end side of said ligation member to an other position in which said tubular member closes at least a part of said gap portion from said front hole side to permit to prevent said ligature received in said side holes from coming off said side holes through said gap portion.

9. The ligator as claimed in claim 8, wherein:

said ligation member is provided at said one end portion of said ligation member with two portions facing tip end portions of said pair of arcuate projections through said gap portion at least one of said two portions having another recess connecting smoothly a prescribed portion of an end surface of said ligation member facing said gap portion and the outer surface of said ligation member, said another recess being formed by chamfering said prescribed portion of said end surface of said ligation member toward the outer surface of the other end side of said ligation member.

10. The ligator as claimed in claim 7, wherein:

said ligation member is provided at said one end portion of said ligation member with two portions facing tip end portions of said pair of arcuate projections through said gap portion, at least one of said two portions having another recess connecting smoothly a prescribed portion of an end surface of said ligation member facing said gap portion and the outer surface of said ligation member, said other recess being formed by chamfering said prescribed portion of said end surface of said ligation member toward the outer surface of the other end side of said ligation member.

11. The ligator as claimed in claim 7, further comprising:

an opening or closing member, which is mounted on to said ligation member, said opening or closing member being movable to a position in which a part of said opening or closing member fits into said gap portion to close at least a part of said gap portion to prevent said ligature received in said side holes from coming off said side holes through said gap portion.

12. A ligator comprising:

a ligation member formed of a bar-shaped body having a constant thickness in a region extending by at least a prescribed length from one end of said ligation member;

a front hole formed on one end surface of said ligation member, said front hole having a prescribed shape and a prescribed depth in a longitudinal direction of said ligation member;

a pair of side holes formed on opposite positions at one end portion of said ligation member so as to be substantially at right angles to said front hole, said front hole being located between said opposite positions, and said side holes communicating with said front hole, opposite ends of a ligature to be knotted passing through said front hole and said side holes, wherein:

said ligation member is provided with a pair of recesses each connecting smoothly an inner surface of each of said side holes of said ligation member and an outer surface of said ligation member, each of said recesses being formed by chamfering an edge portion from said inner surface to said outer surface toward an other end of said ligation member, wherein:

said ligation member is provided with a gap portion, which causes said front hole to communicate with said side holes, said gap portion being formed by cutting a prescribed portion out of said ligation member, which faces said front hole and said side holes formed at the one end portion of said ligation member and extends from the inner surface to the outer surface, said gap portion permitting said ligature to be received in said front hole and said side holes or removed therefrom, wherein said ligation member is formed into a cylindrical shape having a hollow portion in said region extending by said at least a prescribed length said hollow portion forming said from hole, and wherein:

said gap portion is formed by cutting partially out of a peripheral portion of said ligation member, which comes into contact with said front hole and extends from one of said side holes to an other of said side holes, and then removing at least a part of an end peripheral portion of said ligation member, which is placed along said peripheral portion thus cut, thereby said end peripheral portion forming a pair of arcuate projection.

13. The ligator as claimed in claim 12, wherein:

said front hole extends beyond a position of each of said side holes by a prescribed length toward the other end side of said ligation member; and said ligator further comprises an inner Lute, which is formed of a tubular member having a prescribed cross-section, which can be inserted into said front hole, said inner tube being slidably received in said front hole in the longitudinal direction of said ligation member from a position in which a front end of said tubular member is placed beyond said gap portion to reach the other end side of said ligation member to an other position in which said tubular member closes at least a part of said gap portion from said front hole side to permit to prevent said ligature received in said side holes from coming off said side holes through said gap portion.

14. The ligator as claimed in claim 13, wherein:

said ligation member is provided at said one end portion of said ligation member with two portions facing tip end portions of said pair of arcuate projections through said gap portion, at least one of said two portions having an other recess connecting smoothly a prescribed portion of an end surface of said ligation member facing said gap portion and the outer surface of said ligation member, said other recess being formed by chamfering said prescribed portion of said end surface of said ligation member toward the outer surface of the other end side of said ligation member.

15. The ligator as claimed in claim 12, wherein:

said ligation member is provided at said one end portion of said ligation member with two portions facing tip end portions of said pair of arcuate protections through said gap portions at least one of said two portions having another recess connecting smoothly a prescribed portion of an end surface of said ligation member facing said gap portion and the other surface of said ligation member, said another recess being formed by chamfering said prescribed portion of said end surface of said ligation member toward the outer surface of the other end side of said ligation member.

16. The ligator as claimed in claim 12, further comprising:

an opening or closing member, which is mounted on to said ligation member, said opening or closing member being movable to a position in which a part of said opening or closing member fits into said gap portion to close at least a part of said gap portion to prevent said ligature received in said side holes from coming off said side holes through said gap portion.

17. A ligator comprising:

a ligation member formed of a bar-shaped body having a constant thickness in a region extending by at least a prescribed length from one end of said ligation member;

a front hole formed on one end surface of said ligation member, said front hole having a prescribed shape and a prescribed depth in a longitudinal direction of said ligation member; and a pair of side holes formed on opposite positions at one end portion of said ligation member so as to be substantially at right angles to said front hole, said front hole being located between said opposite positions, and said side holes communicating with said front hole, opposite ends of a ligature to be knotted passing through said front hole and said side holes, wherein:

said ligation member is provided with a gap portion, which causes said front hole to communicates with said side holes, said gap portion being formed by cutting a prescribed portion out of said ligation member, which faces said front hole and said side holes formed at the one end portion said ligation member and extends from the inner surface to the outer surface, said gap portion permitting said ligature to be received in said front hole and said side holes or removed therefrom, further comprising:

an opening or closing member, which is mounted on to said ligation member, said opening or closing member being movable to a position in which a part of said opening or closing member fits into said gap portion to close at least a part of said gap portion to prevent said ligature received in said side holes from coming off said side holes through said gap portion.

18. A ligator comprising:

a ligation member formed of a bar-shaped body having a constant thickness in a region extending by at least a prescribed length from one end of said ligation member;

a front hole formed on one end surface of said ligation member, said front hole having a prescribed shape and a prescribed depth in a longitudinal direction of said ligation member;

a pair of side holes formed on opposite positions at one end portion of said ligation member so as to be substantially at right angles to said front hole, said front hole being located between said opposite positions, and said side holes communicating with said front hole, opposite ends of a ligature to be knotted passing through said front hole and said side holes, wherein:

said ligation member is provided with a pair of recesses each connecting smoothly an inner surface of each of said side holes of said ligation member and an outer surface of said ligation member, each of said recesses being formed by chamfering an edge portion from said inner surface to said outer surface toward an other end of said ligation member, wherein:

said ligation member is provided with a gap portion, which causes said front hole to communicate with said side holes, said gap portion being formed by cutting a prescribed portion out of said ligation member, which faces said front hole and said side holes formed at the one end portion of said ligation member and extends from the inner surface to the outer surface, said gap portion permitting said ligature to be received in said front hole arid said side holes or removed therefrom, and wherein, further comprising:

an opening or closing member, which is mounted onto said ligation member, said opening or closing member being movable to a position in which a part of said opening or closing member fits into said gap portion to close at least a part of said gap portion to prevent said ligature received in said side holes from corning off said side holes through said gap portion.

19. A ligator comprising:

a ligation member formed of a bar-shaped body having a constant thickness in a region extending by at least a prescribed length from one end of said ligation member;

a front hole formed on one end surface of said ligation member, said front hole having a prescribed shape and a prescribed depth in a longitudinal direction of said ligation member;

a pair of side holes formed on opposite positions at one end portion of said ligation member so as to be substantially at right angles to said front hole, said front hole being located between said opposite positions, and said side holes communicating with said front hole, opposite ends of a ligature to be knotted passing through said front hole and said side holes, wherein:

said ligation member is provided with a gap portion, which causes said front hole to communicate with said side holes, said gap portion being formed by cutting a prescribed portion out of said ligation member, which faces said front hole and said side holes formed at the one end portion said ligation member and extends from the inner surface to the outer surface, said gap portion permitting said ligature to be received in said front hole and said side holes or removed therefrom, wherein said ligation member is formed into a cylindrical shape having a hollow portion in said region extended by said at least prescribed length, said hollow portion forming said front hole, further comprising:

an opening or closing member, which is mounted on to said ligation member, said opening or closing member being movable to a position in which a part of said opening or closing member fits into said gap portion to close at least a part of said gap portion to prevent said ligature received in said side holes from coming off said side holes through said gap portion.

20. A ligator comprising:

a ligation member formed of a bar-shaped body having a constant thickness in a region extending by at least a prescribed length from one end of said ligation member;

a front hole formed on one end surface of said ligation member, said front hole having a prescribed shape and a prescribed depth in a longitudinal direction of said ligation member;

a pair of side holes formed on opposite positions at one end portion of said ligation member so as to be substantially at right angles to said front hole, said front hole being located between said opposite positions, and said side holes communicating with said front hole, opposite ends of a ligature to be knotted passing through said front hole and said side holes, wherein:

said ligation member is provided with a pair of recesses each connecting smoothly an inner surface of each of said side holes of said ligation member and an outer surface of said ligation member, each of said recesses being formed by chamfering an edge portion from said inner surface to said outer surface toward an other end of said ligation member, wherein:

said ligation member is provided with a gap portion, which causes said front hole to communicate with said side holes, said gap portion being formed by cutting a prescribed portion Out of said ligation member, which faces said front hole and said side holes formed at the one end portion of said ligation member and extends from the inner surface to the outer surface, said gap portion permitting said ligature to be received in said front hole and said side holes or removed therefrom, wherein said ligation member is formed into a cylindrical shape having a hollow portion in said region extending by said at least a prescribed length said hollow portion forming said from hole, and further comprising:

an opening or closing member, which is mounted on to said ligation member, said opening or closing member being movable to a position in which a cart of said pending or closing member fits into said gap portion to close at least a part of said gap portion to prevent said ligature received in said side holes from coming off said side holes through said gap portion.

* * * * *

UNITED STATES PATENT AND TRADEMARK OFFICE
CERTIFICATE OF CORRECTION

PATENT NO. : 6,755,844 B2
DATED : June 29, 2004
INVENTOR(S) : Akihito Furusawa

It is certified that error appears in the above-identified patent and that said Letters Patent is hereby corrected as shown below:

Column 19,
Line 45, "communicates" should read -- communicate --.

Column 20,
Line 38, "cones" should read -- comes --.
Line 44, "out" should read -- cut --.

Column 21,
Line 62, "from" should read -- front --.

Column 22,
Line 7, "projection" should read -- projections --.
Line 11, "Lute" should read -- tube --.
Line 42, "other" should read -- outer --.

Column 23,
Line 6, "communicates" should read -- communicate --.
Line 57, "arid" should read -- and --.

Column 24,
Line 66, "Out" should read -- out --.

Column 25,
Line 8, "from" should read -- front --.

UNITED STATES PATENT AND TRADEMARK OFFICE
CERTIFICATE OF CORRECTION

PATENT NO. : 6,755,844 B2
DATED : June 29, 2004
INVENTOR(S) : Akihito Furusawa

It is certified that error appears in the above-identified patent and that said Letters Patent is hereby corrected as shown below:

<u>Column 26,</u>
Line 4, "cart" should read -- part --.

Signed and Sealed this

Sixth Day of September, 2005

JON W. DUDAS
*Director of the United States Patent and Trademark Office*